(12) United States Patent
Wham et al.

(10) Patent No.: US 12,295,690 B2
(45) Date of Patent: May 13, 2025

(54) SYSTEMS AND METHODS LEVERAGING AUDIO SENSORS TO FACILITATE SURGICAL PROCEDURES

(71) Applicant: Covidien LP, Mansfield, MA (US)

(72) Inventors: Robert H. Wham, Boulder, CO (US); William E. Robinson, Boulder, CO (US); James D. Allen, IV, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 388 days.

(21) Appl. No.: 17/734,150

(22) Filed: May 2, 2022

(65) Prior Publication Data

US 2022/0395344 A1 Dec. 15, 2022

Related U.S. Application Data

(60) Provisional application No. 63/210,622, filed on Jun. 15, 2021.

(51) Int. Cl.
*A61B 34/00* (2016.01)
*A61B 17/00* (2006.01)
*A61B 34/37* (2016.01)

(52) U.S. Cl.
CPC .............. *A61B 34/70* (2016.02); *A61B 34/25* (2016.02); *A61B 34/37* (2016.02); *A61B 2017/00119* (2013.01)

(58) Field of Classification Search
CPC ......... A61B 34/70; A61B 34/25; A61B 34/37; A61B 2017/00119
See application file for complete search history.

(56) References Cited

U.S. PATENT DOCUMENTS

| | | | |
|---|---|---|---|
| 5,776,130 A | 7/1998 | Buysse et al. | |
| 7,766,910 B2 | 8/2010 | Hixson et al. | |
| 8,226,650 B2 | 7/2012 | Kerr | |
| 10,391,235 B2 | 8/2019 | Schabbach et al. | |
| 10,517,627 B2 | 12/2019 | Timm et al. | |
| 10,886,015 B2 | 1/2021 | Wolf et al. | |
| 2001/0031975 A1 | 10/2001 | Whitman | |
| 2002/0049454 A1 | 4/2002 | Whitman et al. | |
| 2003/0204184 A1* | 10/2003 | Ferek-Patric | A61B 18/1492 606/41 |
| 2009/0292283 A1 | 11/2009 | Odom | |
| 2010/0298705 A1 | 11/2010 | Pelissier et al. | |
| 2012/0172873 A1 | 7/2012 | Artale et al. | |
| 2012/0184988 A1 | 7/2012 | Twomey et al. | |
| 2013/0345541 A1 | 12/2013 | Nau, Jr. | |
| 2014/0278388 A1 | 9/2014 | Watson et al. | |
| 2016/0074092 A1 | 3/2016 | Joseph | |

(Continued)

*Primary Examiner* — Fan S Tsang
*Assistant Examiner* — David Siegel

(57) ABSTRACT

A surgical system includes at least one audio sensor configured to sense audio during a surgical procedure and to output audio data based on the sensed audio. The surgical system further includes a computing device operably coupled to the at least one audio sensor and configured to receive the output audio data from the at least one audio sensor. The computing device includes a processor and memory storing instructions that, when executed by the processor, cause the processor to determine at least one of a cause or a location of a sound based at least on the output audio data and to output an indication of the at least one of the cause or location of the sound.

20 Claims, 13 Drawing Sheets

(56) References Cited

U.S. PATENT DOCUMENTS

| | | |
|---|---|---|
| 2016/0143685 A1 | 5/2016 | Friedrichs |
| 2017/0296278 A1 | 10/2017 | Whitman et al. |
| 2019/0125453 A1 | 5/2019 | Krimsky et al. |
| 2019/0125456 A1 | 5/2019 | Shelton, IV et al. |
| 2019/0200863 A1 | 7/2019 | Shelton, IV et al. |
| 2019/0201115 A1 | 7/2019 | Shelton, IV et al. |
| 2019/0206003 A1 | 7/2019 | Harris et al. |
| 2020/0093459 A1* | 3/2020 | Rahman ............... A61B 5/7275 |
| 2020/0314569 A1 | 10/2020 | Morgan et al. |
| 2020/0330066 A1* | 10/2020 | Cromwell ............ A61B 5/7203 |
| 2020/0367913 A1 | 11/2020 | Forstein et al. |
| 2020/0394994 A1* | 12/2020 | Prenger ................. G06N 3/045 |
| 2021/0205031 A1 | 7/2021 | Shelton, IV et al. |
| 2021/0212775 A1 | 7/2021 | Shelton, IV et al. |
| 2021/0322020 A1 | 10/2021 | Shelton, IV et al. |
| 2022/0000484 A1 | 1/2022 | Shelton, IV et al. |

* cited by examiner

1100

1100

SYSTEMS AND METHODS LEVERAGING AUDIO SENSORS TO FACILITATE SURGICAL PROCEDURES

CROSS-REFERENCE TO RELATED APPLICATION

This application claims the benefit of, and priority to, U.S. Provisional Patent Application No. 63/210,622, filed on Jun. 15, 2021, the entire contents of which are hereby incorporated herein by reference.

BACKGROUND

Technical Field

The present disclosure relates to surgery and, more specifically, to systems and methods leveraging audio sensors to facilitate surgical procedures.

Background of Related Art

Endoscopic surgical procedures are advantageous in that they reduce patient discomfort, recovery time, etc. However, endoscopic surgical procedures are challenging in that the surgeon is not able to directly rely on visual, audio, and/or tactile senses to monitor progress of the surgical procedure, guide surgical instrumentation, determine the location and condition of tissue, perform surgical tasks, etc. Rather, the surgeon is required to rely on feedback data, e.g., a video feed, sensor data, etc., in order to monitor progress of the surgical procedure, guide surgical instrumentation, determine the location and condition of tissue, perform surgical tasks, etc.

Robotic surgical procedures are also advantageous in that they allow for increased dexterity and precise movements and also because they allow a surgeon to operate on a patient from a remote location. However, robotic surgical procedures, including endoscopic robotic surgical procedures, likewise present challenges in that they require the surgeon to rely on feedback data rather than directly relying on visual, audio, and/or tactile senses.

SUMMARY

As used herein, the term "distal" refers to the portion that is being described which is farther from an operator (whether a human surgeon or a surgical robot), while the term "proximal" refers to the portion that is being described which is closer to the operator. Terms including "generally," "about," "substantially," and the like, as utilized herein, are meant to encompass variations, e.g., manufacturing tolerances, material tolerances, use and environmental tolerances, measurement variations, design variations, and/or other variations, up to and including plus or minus 10 percent. Further, to the extent consistent, any or all of the aspects detailed herein may be used in conjunction with any or all of the other aspects detailed herein.

Provided in accordance with aspects of the present disclosure is a surgical system including at least one audio sensor configured to sense audio during a surgical procedure and to output audio data based on the sensed audio. The surgical system further includes a computing device operably coupled to the at least one audio sensor and configured to receive the output audio data from the at least one audio sensor. The computing device includes a processor and memory storing instructions that, when executed by the processor, cause the processor to determine at least one of a cause or a location of a sound based at least on the output audio data, and output an indication of the at least one of the cause or location of the sound.

In an aspect of the present disclosure, the processor is caused to determine the location of the sound within an internal surgical site based on the output audio data. In such aspects, outputting the indication of the location of the sound includes displaying, on a display providing a video image of the internal surgical site, an icon overlaid over the video image of the internal surgical site at a location on the video image corresponding to the location of the sound.

In another aspect of the present disclosure, the processor is caused to determine the cause of the sound output an indication of the cause of the sound.

In still another aspect of the present disclosure, the at least one audio sensor includes at least one audio sensor disposed within an internal surgical site and/or at least one audio sensor disposed external of the internal surgical site. In aspects, the at least one audio sensor includes a plurality of audio sensors including at least one audio sensor disposed within an internal surgical site and/or at least one audio sensor disposed external of the internal surgical site.

In yet another aspect of the present disclosure, the processor is caused to determine the at least one of the cause or the location of the sound based on the output audio data and additional data including at least one of stored data, location data, or feedback data.

In still yet another aspect of the present disclosure, the processor is caused to convert at least a portion of the output audio data into image data and to determine the cause of the sound based on the image data.

Another surgical system provided in accordance with aspects of the present disclosure includes a plurality of audio sensors and a computing device. The plurality of audio sensors includes at least one audio sensor configured for positioning within an internal surgical site and at least one other audio sensor configured for positioning external of the internal surgical site. Each audio sensor of the plurality of audio sensors is configured to sense audio and to output audio data based on the sensed audio. The computing device is operably coupled to the plurality of audio sensors and configured to receive the output audio data from each audio sensor of the plurality of audio sensors. The computing device includes a processor and memory storing instructions that, when executed by the processor, cause the processor to determine at least one of a cause or a location of a sound based at least on the output audio data and control operation of at least one surgical instrument based on the determined at least one of cause or location of the sound.

In an aspect of the present disclosure, at least one audio sensor of the plurality of audio sensors is disposed on or incorporated into a surgical instrument configured to perform a task within the internal surgical site.

In another aspect of the present disclosure, the processor is caused to determine both the cause and the location of the sound based at least on the output audio data.

In still another aspect of the present disclosure, the processor is caused to determine the at least one of the cause or the location of the sound based on the output audio data and additional data including at least one of stored data, location data, or feedback data.

In yet another aspect of the present disclosure, the processor is caused to convert at least a portion of the output audio data into image data and to determine the cause of the sound based on the image data.

In still yet another aspect of the present disclosure, the processor is caused to control operation of the at least one surgical instrument by outputting a signal to inhibit actuation or activation of the at least one surgical instrument.

Another surgical system provided in accordance with the present disclosure includes at least one audio sensor configured to sense audio during a surgical procedure and to output audio data based on the sensed audio. The surgical system further includes a computing device operably coupled to the at least one audio sensor and configured to receive the output audio data from the at least one audio sensor. The computing device includes a processor and memory storing instructions that, when executed by the processor, cause the processor to convert at least a portion of the output audio data into image data, determine a cause of a sound in the at least a portion of the output audio data based on the image data, and output at least one of an indicator or a control signal based on the determined cause of the sound.

In an aspect of the present disclosure, converting the at least a portion of the output audio data into the image data includes applying a melody Short-Time Fourier Transform to the at least a portion of the output audio data to obtain a melody spectrogram as the image data. In other aspects, converting the at least a portion of the output audio data into the image data includes a wavelet transform or wavelet scattering, e.g., to convert 1D audio data into 2D image data. In still other aspects, two audio waveforms may be plotted on a graph, e.g., where one represents the Y coordinates and the other the X coordinates, thus resulting in image data in the form of a 2D X-Y plot. In yet other aspects, audio data from multiple audio sensors may be utilized to create a multi-dimensional matrix that mimics image data.

In another aspect of the present disclosure, determining the cause of the sound based on the image data includes implementing a convolutional neural network (CNN). In other aspects, other neural networks may be utilized. A neural network (a CNN or other neural network) or any other suitable machine learning or traditional algorithm may additionally or alternatively be utilized for location determination, for example, using data from two or more audio sensors and comparing the signal phase, amplitude, and frequency response, e.g., for triangulation.

In still another aspect of the present disclosure, the processor is caused to output the control signal based on the determined cause of the sound and the control signal is configured to inhibit actuation of at least one surgical instrument, inhibit activation of at least one surgical instrument, and/or change an operating parameter (e.g., an energy setting) of at least one surgical instrument.

In yet another aspect of the present disclosure, the processor is caused to select the at least a portion of the output audio data to be converted based at least on a detection of the sound and/or additional input data.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

In the following description, well-known functions or constructions are not described in detail to avoid obscuring the present disclosure in unnecessary detail. Those skilled in the art will understand that the present disclosure may be adapted for use with either an endoscopic instrument, a laparoscopic instrument, an open instrument, or as part of a robotic surgical system. It should also be appreciated that different electrical and mechanical connections and other considerations may apply to each particular type of instrument or system.

Figure 1:
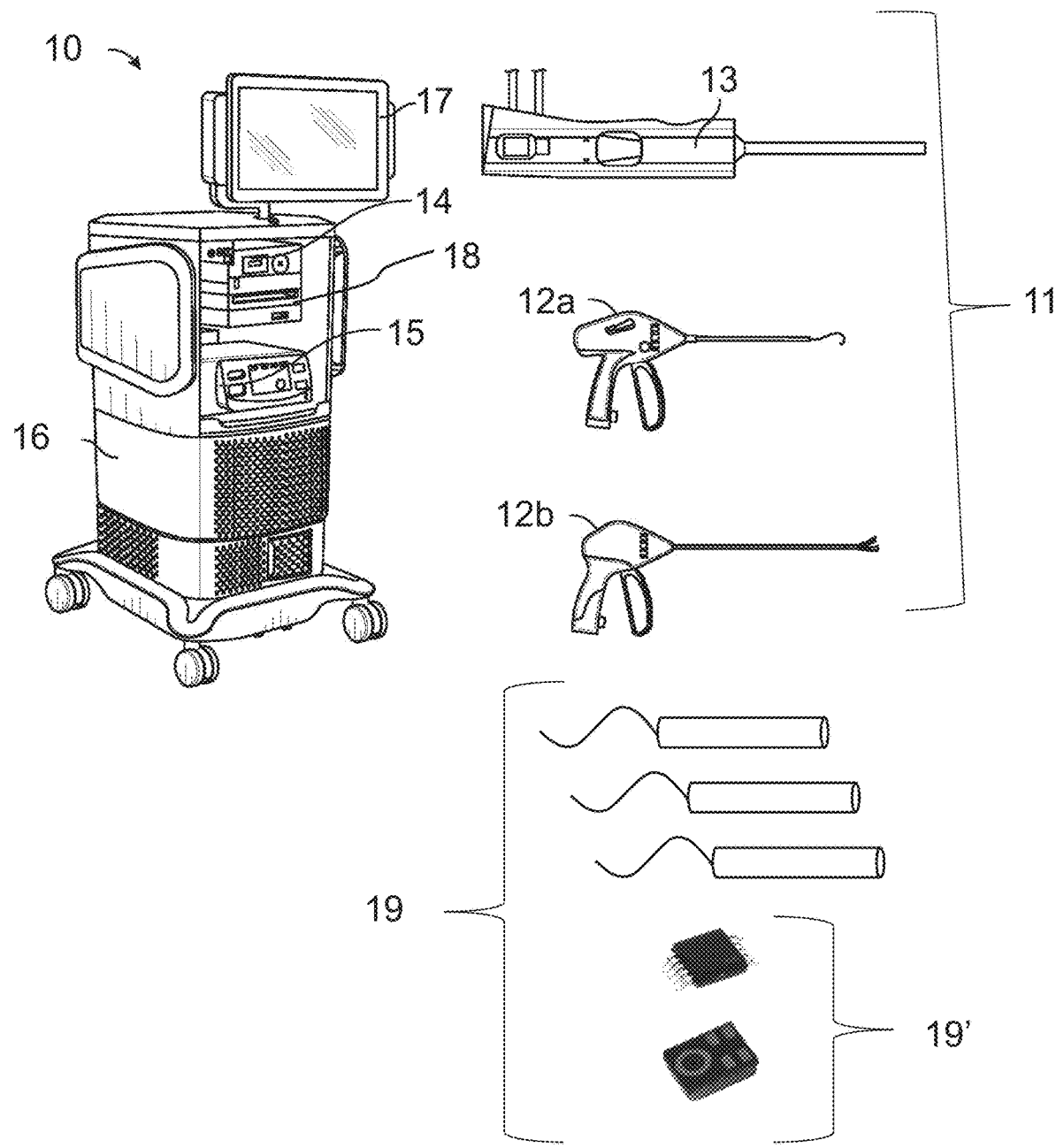
FIG. 1 is a perspective view of a surgical system provided in accordance with aspects of the present disclosure.

Referring to FIG. 1, a surgical system 10 provided in accordance with the present disclosure is shown including at least one surgical instrument 11, a surgical controller 14 configured to connect to one or more of the at least one surgical instrument 11, a surgical generator 15 configured to connect to one or more of the at least one surgical instrument 11, a control tower 16 housing the surgical controller 14 and the surgical generator 15, and a display 17 disposed on control tower 16 and configured to output, for example, video and/or other imaging data from one or more of the at least one surgical instrument 11 and to display operating parameter data, feedback data, etc. from one or more of the at least one surgical instrument 11 and/or generator 15. Display 17 and/or a separate user interface (not shown) may be provided to enable user input, e.g., via a keyboard, mouse, touch-screen GUI, etc.

The at least one surgical instrument 11 may include, for example, a first surgical instrument 12a for manipulating and/or treating tissue, a second surgical instrument 12b for manipulating and/or treating tissue, and/or a third surgical instrument 13 for visualizing and/or providing access to an internal surgical site. The first and/or second surgical instruments 12a, 12b may include: energy-based surgical instruments for grasping, sealing, and dividing tissue such as, for example, an electrosurgical forceps (detailed below), an ultrasonic clamp-based instrument (detailed below), etc.; energy-based surgical instruments for tissue dissection, resection, ablation and/or coagulation such as, for example, an electrosurgical pencil, a resection wire, an ablation (microwave, radiofrequency, cryogenic, etc.) device, etc.; mechanical surgical instruments configured to clamp and close tissue such as, for example, a surgical stapler, a surgical clip applier, etc.; mechanical surgical instruments configured to facilitate manipulation and/or cutting of tissue such as, for example, a surgical grasper, surgical scissors, a surgical retractor, etc.; and/or any other suitable surgical instruments. Although first and second surgical instruments 12a, 12b are shown in FIG. 1, greater or fewer of such instruments 12a, 12b are also contemplated.

The third surgical instrument 13 may include, for example, an endoscope or other suitable surgical camera to enable visualizing into an internal surgical site such as, for example, video imaging, thermal imaging, ultrasound imaging, etc. The third surgical instrument 13 may additionally or alternatively include one or more access channels to enable insertion of first and second surgical instruments 12a, 12b, aspiration/irrigation, insertion of any other suitable surgical tools, etc. The third surgical instrument 13 may be coupled, via wired or wireless connection, to controller 14 for processing the video (or other imaging) data for displaying the same on display 17. Although one third surgical instrument 13 is shown in FIG. 1, more of such instruments 13 are also contemplated; alternatively, third surgical instrument 13 may be omitted.

Continuing with reference to FIG. 1, surgical system 10 further includes a computing device 18, which is in wired or wireless communication with one or more of the at least one surgical instrument 11, generator 15, and/or display 17. Computing device 18 is capable of receiving data from one or more of the at least one surgical instrument 11, e.g., activation data, actuation data, feedback data, etc., from first and/or second instruments 12a, 12b, and/or video (or other imaging) data from another one of the at least one surgical instrument 11, e.g., third instrument 13. Computing device 18 may process the video (or other imaging) data substantially at the same time upon reception of the data, e.g., in real time. Further, computing device 18 may be capable of providing desired parameters to and/or receiving feedback data from first and/or second instruments 12a, 12b, surgical generator 15 (for implementation in the control of surgical instruments 12a, 12b, for example), and/or other suitable devices in real time to facilitate feedback-based control of a surgical operation and/or output of suitable display information for display on display 17, e.g., beside, together with, as an overlay on, etc., the video image. Computing device 18 is described in greater detail below.

Figure 3A:
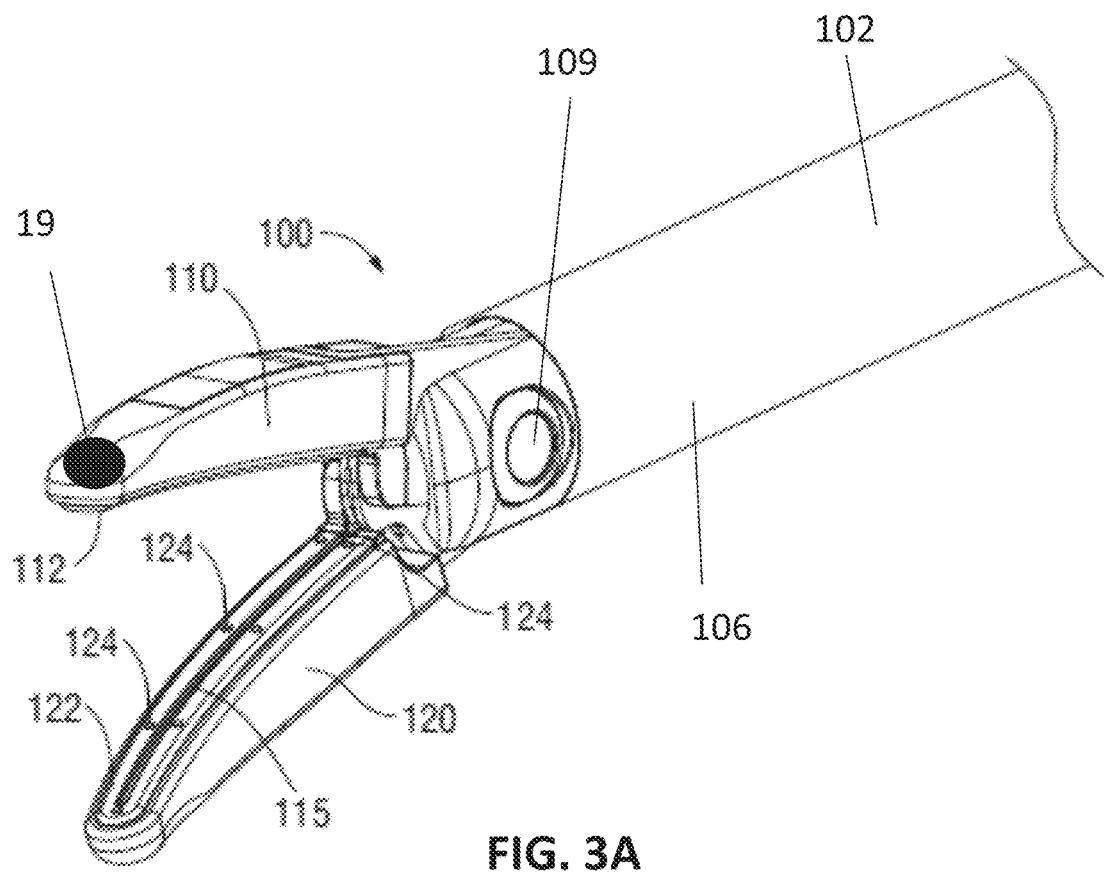
FIGS. 3A and 3B are perspective views of an end effector assembly of an electrosurgical instrument provided in accordance with aspects of the present disclosure wherein jaw members of the end effector assembly are disposed in spaced-apart and approximated positions, respectively.
Figure 3B:
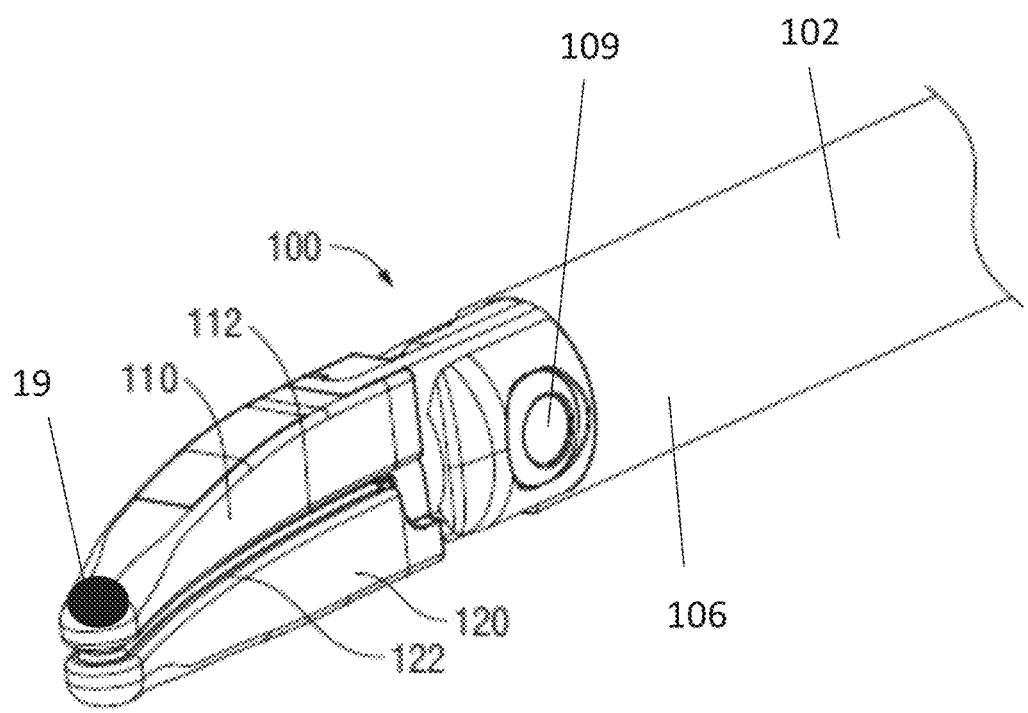
Figure 4:
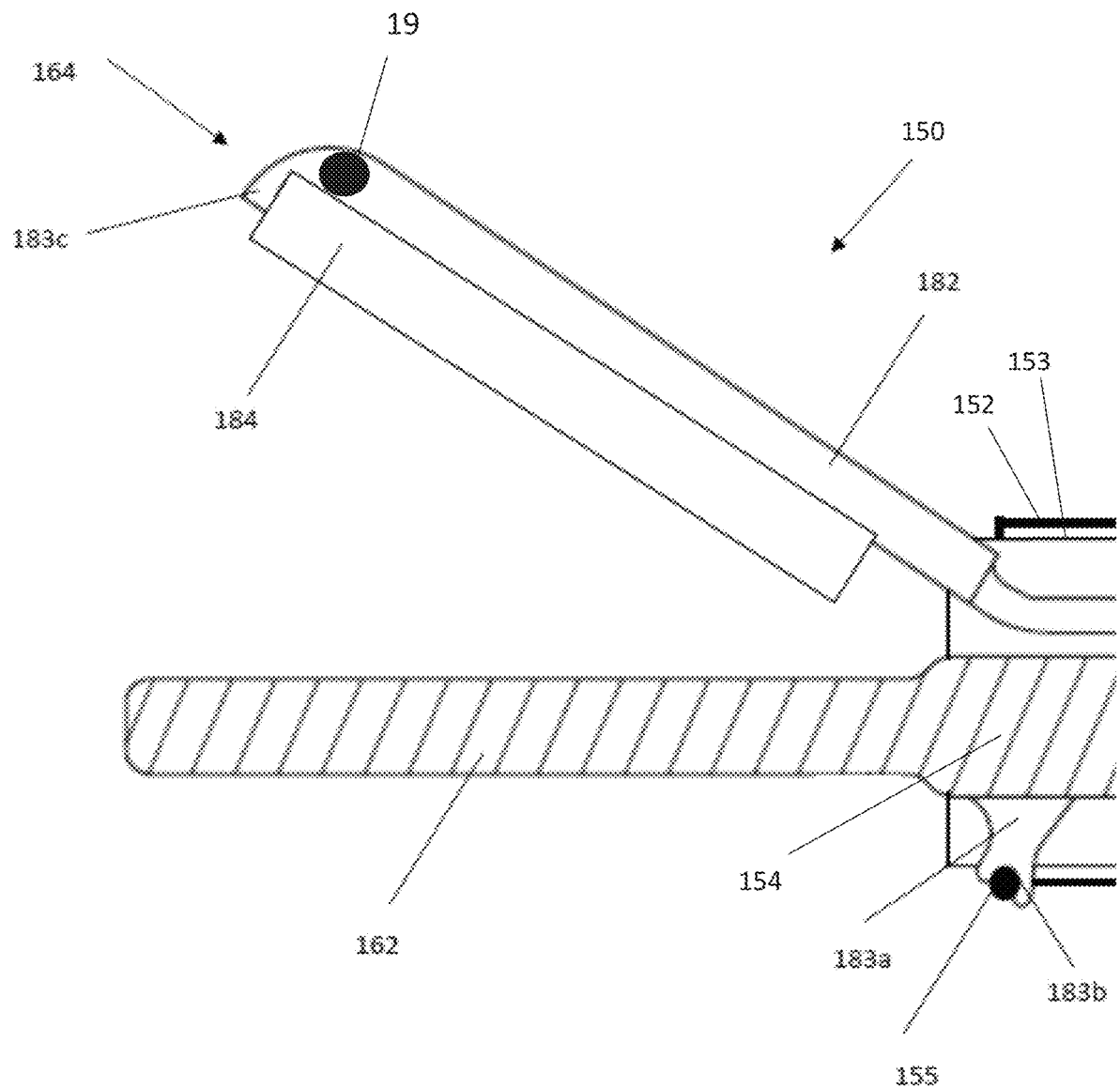
FIG. 4 is a longitudinal, cross-sectional view of an end effector assembly of an ultrasonic surgical instrument provided in accordance with aspects of the present disclosure.

Surgical system 10 also includes at least one audio sensor device 19, e.g., a microphone or microphones, which may be standalone device(s) (as shown in FIG. 1) and/or which may be incorporated (permanently or detachably) on or within one or more of the at least one surgical instrument 11 (see FIGS. 3A-4). One or more of the at least one audio sensor device 19 may be configured for positioning external of an internal surgical site, e.g., on an operating table, on an external portion (e.g., a handle or mounting portion) of one or more of the at least one surgical instrument 11, on an electrosurgical generator, as a stand-alone device, etc. One or more of the at least one audio sensor device 19 may be configured for insertion into an internal surgical site, e.g., as a separate probe device, on or adjacent the end effector assembly of one or more of the at least one surgical instrument 11, etc. The at least one audio sensor device 19 is thus capable of sensing audio internally within the internal surgical site and/or within the operating room externally of the internal surgical site. The at least one audio sensor device 19 may be coupled to a speaker or other audio-providing device of system 10 to broadcast the sensed audio. Alternatively or additionally, the at least one audio sensor device 19 is coupled to computing device 18 (or other suitable computing device), via wired or wireless connections, to, as detailed below, enable processing of the sensed audio data and providing of a suitable output of a different form, e.g., outputting, to display 17, a visual indication of the type and/or location of audio detected, and/or for controlling surgical system 10 in accordance therewith.

In configurations where multiple audio sensor devices 19 are provided, the audio sensor devices 19 may be disposed at different locations and/or may be configured to sense different audio frequency ranges. Suitable audio sensor devices 19, particularly those for use within an internal surgical site and/or attached to or incorporated within one or more of the at least one surgical instrument 11, include MEMS microphones 19', although other suitable audio sensor devices 19 are also contemplated. Other input devices may be provided in addition to or as an alternative to one or more of the at least one audio sensor device 19 such as, for example, at least one accelerometer configured to sense vibrations.

Figure 2:
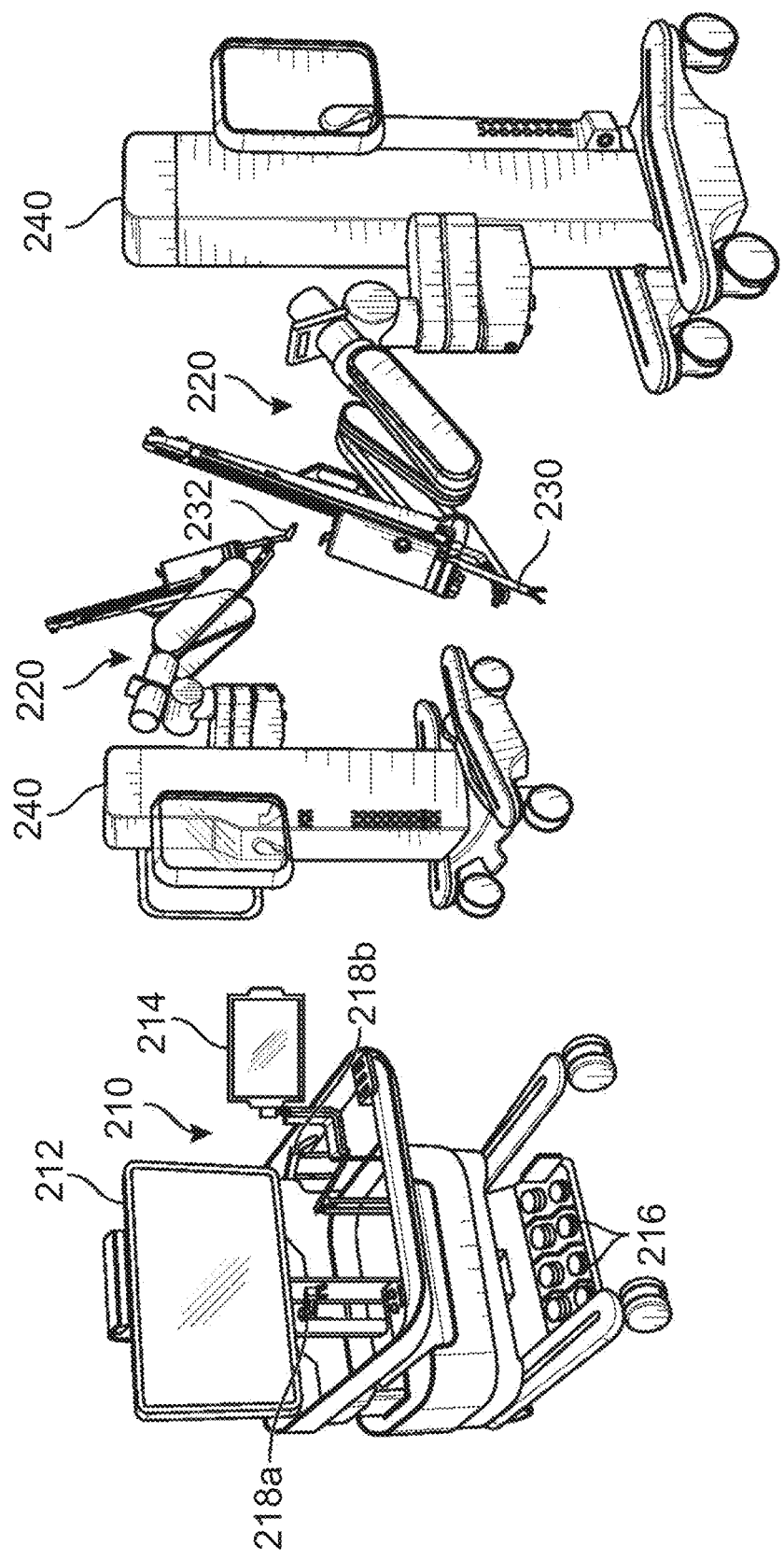
FIG. 2 is a perspective view of a robotic surgical system provided in accordance with aspects of the present disclosure.

With additional reference to FIG. 2, a robotic surgical system 200 is shown. Surgical system 10 of FIG. 1 may be used as part of robotic surgical system 200 and, thus, robotic surgical system 200 may include any of the features thereof as detailed above or otherwise herein. Control tower 16 may be also connected to one or more of the components of robotic surgical system 200, which includes a surgical console 210 and one or more robotic arms 220. Each robotic arm 220 may include a surgical instrument 230 (e.g., one of first or second instruments 12a, 12b) removably coupled thereto. Each of robotic arm 220 may be also coupled to a movable cart 240. Audio sensor devices 19 may be disposed on one or more of surgical instruments 230 or separately therefrom.

A camera 232 (e.g., third instrument 13 of FIG. 1) may be coupled to one of robotic arms 220. An audio sensor device 19 may be disposed on camera 232 or separately therefrom. Camera 232 is configured to capture live images (e.g., video stream, thermal, ultrasound, and/or other imaging) of the surgical site. Surgical console 210 may include a first display 212, which displays a video feed of the surgical site provided by camera 232, and a second interaction display 214, which displays a user interface for controlling robotic surgical system 200. First and second displays 212 and 214 may be touchscreens allowing for displaying various graphical user interfaces and receiving inputs from users.

Surgical console 210 may include a plurality of user interface devices, such as pedals 216 and a pair of handle controllers 218a and 218b, which are used by a user to remotely control robotic arms 220. Surgical console 210 may further include an armrest used to support a user's arms while operating handle controllers 218a and 218b.

Control tower 16 may act as an interface between surgical console 210 and one or more robotic arms 220. In particular, control tower 16 may be configured to control robotic arms 220, such as to move robotic arms 220 and the corresponding surgical instruments 230, based on a set of programmable instructions and/or input commands from surgical console 210, in such a way that robotic arms 220 and surgical instruments 230 execute a desired movement sequence in response to input from foot pedals 216 and handle controllers 218a and 218b.

Each of control tower 16, surgical console 210, and robotic arms 220, which are interconnected to each other using any suitable communication network based on wired or wireless communication protocols, may include a respective or collective computing device. The computing device(s) may include any suitable processor(s) operably connected to a memory(s).

Turning to FIGS. 3A and 3B, in aspects, the at least one surgical instrument 11 (FIG. 1) may include an electrosurgical forceps configured for sealing and dividing tissue, an end effector assembly 100 of which is illustrated in FIGS. 3A and 3B. The electrosurgical forceps may define any suitable configuration such as, for example, a shaft-based manual device, a hemostat-style manual device, a partly powered device (shaft-based or hemostat-style), a fully powered shaft-based device, a robotic device, etc.

Continuing with reference to FIGS. 3A and 3B, the electrosurgical forceps includes a shaft 102 that supports end effector assembly 100 at a distal end portion 106 thereof. A drive assembly (not shown) extending through shaft 102 operably coupled to end effector assembly 100 to impart movement of one or both of jaw members 110, 120 of end effector assembly 100 about pivot 109 and relative to the other between a spaced-apart position (FIG. 3A) and an approximated position (FIG. 3B) to grasp tissue therebetween upon actuation of the drive assembly. Suitable mechanisms for use as or in conjunction with the drive assembly for supplying and/or controlling a clamping force applied to tissue grasped between jaw members 110, 120 include those described in U.S. Pat. Nos. 5,776,130; 7,766,910; and 8,226,650; and/or U.S. Patent Application Pub. Nos. 2009/0292283; 2012/0172873; and 2012/0184988, the entire contents of all of which are hereby incorporated by reference herein. Other suitable mechanisms for applying a specific clamping force or clamping force within a specific clamping force range to tissue grasped between jaw members 110, 120 may also be provided.

Each jaw member 110, 120 of end effector assembly 100 includes an electrically conductive tissue contacting surface 112, 122, respectively, that cooperate to grasp tissue therebetween, e.g., in one or more approximated positions of jaw members 110, 120, and to facilitate sealing the grasped tissue via conducting the energy from generator 15 (FIG. 1) therebetween. More specifically, tissue contacting surfaces 112, 122 are electrically coupled to generator 15 (FIG. 1) and are configured to be energized to different potentials to enable the conduction of Radio Frequency (RF) electrosurgical energy provided by generator 15 (FIG. 1) between tissue contacting surfaces 112, 122 and through tissue grasped therebetween to seal tissue. Tissue contacting surfaces 112, 122 may be defined by electrically conductive plates secured to jaw members 110, 120, may be defined by surfaces of jaw members 110, 120 themselves, may be formed via the deposition of material onto jaw members 110, 120, or may be defined and/or formed in any other suitable manner.

Either or both jaw members 110, 120 may further include one or more stop members 124 (FIG. 2A) disposed on or otherwise associated with either or both tissue-contacting surface 112, 122 to maintain a minimum gap distance between tissue contacting surfaces 112, 122 when jaw members 110, 120 are disposed in a fully approximated position, thus inhibiting electrical shorting. Stop members 124 may be insulative, partly insulative, and/or electrically isolated from either or both tissue contacting surfaces 112, 122

In some configurations, a knife assembly (not shown) is disposed within shaft 102 and a knife channel 115 is defined within one or both jaw members 110, 120 to permit reciprocation of a knife blade (not shown) therethrough to mechanically cut tissue grasped between jaw members 110, 120. In aspects, the knife blade is energizable to enable dynamic energy-based tissue cutting. Alternatively, end effector assembly 100 may include a static energy-based tissue cutter (not shown), e.g., disposed one or within one of the jaw members 110, 120. The energy-based cutter, whether static or dynamic, may be configured to supply any suitable energy, e.g., RF, microwave, infrared, light, ultrasonic, thermal, etc., to tissue for energy-based tissue cutting.

In aspects, the at least one audio sensor device 19 may include an audio sensor device 19 attached to or incorporated into end effector assembly 100, e.g., on or within jaw member 110 (as shown), on or within jaw member 120, or on or within distal end portion 106 of shaft 102. In such aspects, the attached or incorporated audio sensor device 19 may be a MEMS microphone type audio sensor device 19' (see FIG. 1).

With reference to FIG. 4, in aspects, the at least one surgical instrument 11 (FIG. 1) may include an ultrasonic surgical instrument configured for sealing, dividing, and/or otherwise treating tissue, an end effector assembly 150 of which is illustrated in FIG. 4. The ultrasonic surgical instrument may define any suitable configuration such as, for example, a shaft-based manual device, a hemostat-style manual device, a partly powered device (shaft-based or hemostat-style), a fully powered shaft-based device, a robotic device, etc.

The ultrasonic surgical instrument includes an outer drive sleeve 152, an inner support sleeve 153 disposed within outer drive sleeve 152, a waveguide 154 extending through inner support sleeve 153, and end effector assembly 150 including a blade 162 and a jaw member 164. A drive assembly is operably coupled to outer drive sleeve 152 which, in turn, is operably coupled to jaw member 164. A distal end portion of inner support sleeve 153 pivotably supports jaw member 164. As such, actuation of the ultrasonic surgical instrument moves outer drive sleeve 152 about inner support sleeve 153 to pivot jaw member 164 relative to blade 162 from an open position towards a closed position for clamping tissue between jaw member 164 and blade 162. The configuration of outer and inner sleeves 152, 153 may be reversed, e.g., wherein outer sleeve 152 is the support sleeve and inner sleeve 153 is the drive sleeve. Other suitable drive structures as opposed to a sleeve are also contemplated such as, for example, drive rods, drive cables, drive screws, etc.

The drive assembly may be tuned to provide a jaw clamping force, or jaw clamping force within a jaw clamping force range, to tissue clamped between jaw member 164 and blade 162, such as described in U.S. patent application Ser. No. 17/071,263, filed on Oct. 15, 2020, the entire contents of which are hereby incorporated herein by reference. Alternatively, the drive assembly may include a force limiting feature, e.g., a spring, whereby the clamping force applied to tissue clamped between jaw member 164 and blade 162 is limited to a particular jaw clamping force or a jaw clamping force within a jaw clamping force range, such as described in U.S. Pat. No. 10,368,898, the entire contents of which are hereby incorporated herein by reference.

Continuing with reference to FIG. 4, waveguide 154 includes blade 162 disposed at a distal end thereof. A proximal end portion of waveguide 154 is configured to engage, e.g., in threaded engagement, an ultrasonic transducer (not shown) such that ultrasonic motion produced by the ultrasonic transducer is transmitted along waveguide 154 to blade 162 for treating tissue clamped between blade 162 and jaw member 164 or positioned adjacent to blade 162.

Blade 162, in addition to receiving ultrasonic energy transmitted along waveguide 154 from the ultrasonic transducer 140, may also be adapted to connect to generator 15 (FIG. 1) to enable the supply of RF energy to blade 162 for conduction to tissue in contact therewith. In bipolar configurations, RF energy is conducted between blade 162 and jaw member 164 (or between portions of jaw member 164 and/or blade 162) and through tissue disposed therebetween to treat tissue. In monopolar configurations, RF energy is conducted from blade 162, serving as the active electrode, to tissue in contact therewith and is ultimately returned to generator 15 (FIG. 1) via return electrode device (not shown) serving as the passive or return electrode.

Jaw member 164 of end effector assembly 160 includes more rigid structural body 182 and more compliant jaw liner 184. Structural body 182 may be formed from an electrically conductive material, e.g., stainless steel, and/or may include electrically conductive portions. Structural body 182 includes a pair of proximal flanges 183a that are pivotably coupled to the inner support sleeve 153 via receipt of pivot bosses (not shown) of proximal flanges 183a within corresponding openings (not shown) defined within the inner support sleeve 153 and operably coupled with outer drive sleeve 152 via a drive pin 155 secured relative to outer drive sleeve 152 and pivotably received within apertures 183b defined within proximal flanges 183a. As such, sliding of outer drive sleeve 152 about inner support sleeve 153 pivots jaw member 164 relative to blade 162 from the open position towards the closed position to clamp tissue between jaw liner 184 of jaw member 164 and blade 162.

A distal support portion 183c of structural body 182 captures jaw liner 184 in a cavity defined therein to facilitate receipt and retention therein, although other configurations are also contemplated. Jaw liner 184 is fabricated from an electrically insulative, compliant material such as, for example, polytetrafluoroethylene (PTFE). The compliance of jaw liner 184 enables blade 162 to vibrate while in contact with jaw liner 184 without damaging components of the ultrasonic surgical instrument and without compromising the hold on tissue clamped between jaw member 164 and blade 162. Jaw liner 184 extends from structural body 182 towards blade 162 to inhibit contact between structural body 182 and blade 162 in the closed position of jaw member 164. The insulation of jaw liner 184 maintains electrical isolation between blade 162 and structural body 182 of jaw member 164, thereby inhibiting shorting.

Structural body 182, in aspects, may be adapted to connect to a source of electrosurgical energy, e.g., generator 15 (FIG. 1), and, in a bipolar configuration, is charged to a different potential as compared to blade 162 to enable the conduction of bipolar electrosurgical (e.g., RF) energy through tissue clamped therebetween, to treat the tissue. In a monopolar configuration, structural body 182 may be un-energized, may be charged to the same potential as compared to blade 162 (thus both defining the active electrode), or may be energized while blade 162 is not energized (wherein structural body 182 defines the active electrode). In either monopolar configuration, energy is returned to generator 15 (FIG. 1) via a return electrode device (not shown) which serves as the passive or return electrode.

In aspects, the entirety of structural body 182 of jaw member 164 is connected to generator 15 (FIG. 1). Alternatively, structural body 182 may be formed from or embedded at least partially in an insulative material, e.g., an overmolded plastic. In such configurations, electrically conductive surfaces, e.g., in the form of plates, may be disposed on or captured by the overmolded plastic to define electrodes on either side of jaw liner 184 on the blade facing side of jaw member 164. The electrically conductive surfaces, in such aspects, are connected to generator 15 (FIG. 1) and may be energized for use in bipolar and/or monopolar configurations, e.g., energized to the same potential as one another and/or blade 162 and/or different potentials as one another and/or blade 162.

In aspects, the at least one audio sensor device 19 may include an audio sensor device 19 attached to or incorporated into end effector assembly 150, e.g., on or within jaw member 164 (as shown) or on or within the distal end portion of one of tubes 152, 153. In such aspects, the attached or incorporated audio sensor device 19 may be a MEMS microphone type audio sensor device 19' (see FIG. 1).

Figure 5:
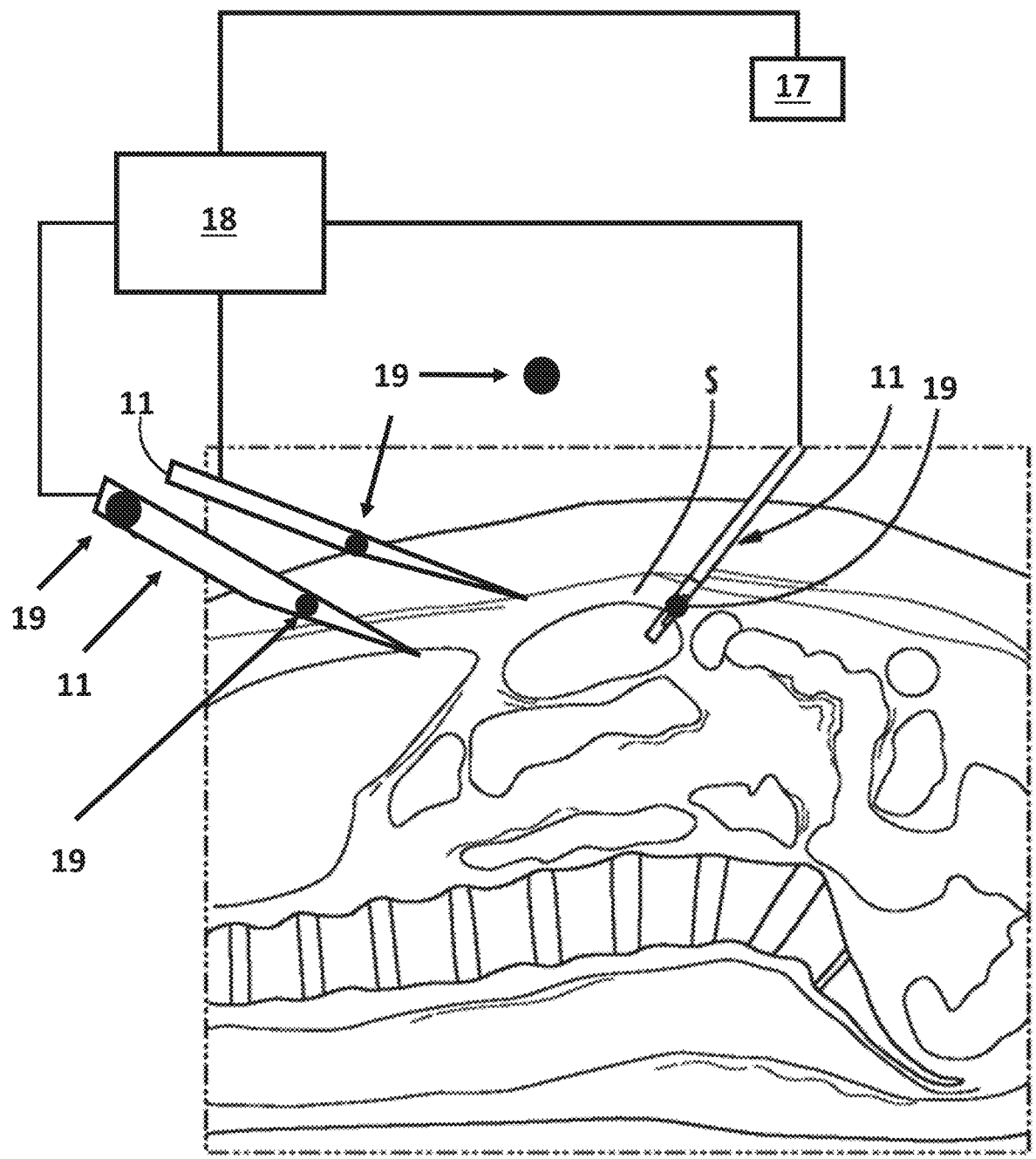
FIG. 5 is a schematic illustration of the surgical system of FIG. 1 in use performing a surgical procedure within an internal surgical site.

Referring to FIG. 5, a portion of surgical system 10 (FIG. 1) is shown in use where a plurality of surgical instruments 11 including audio sensor devices 19 incorporated thereon or therein are disposed within an internal surgical site "S." Further, an audio sensor device 19 is disposed on or within one of the surgical instruments 11 externally of the internal surgical site "S," and another audio sensor device 19 is configured as a standalone device positioned externally of the internal surgical site "S." Although an exemplary arrangement of audio sensor devices 19 is shown in FIG. 5, it is contemplated that any suitable combination of at least one audio sensor device 19 incorporated into at least one surgical instrument 11, independent of the surgical instrument(s) 11, internally disposed within the internal surgical site "S," and/or externally disposed of the internal surgical site "S" may be provided. Each audio sensor device 19 is connected, wired or wirelessly, to computing device 18, which in turn, is connected, wired or wirelessly, to display 17 and/or other components of system 10 (see FIG. 1).

Computing device 18 may include, by way of non-limiting examples, one or more: server computers, desktop computers, laptop computers, notebook computers, Internet appliances, mobile smartphones, tablet computers, personal digital assistants, embedded computers, and the like. Computing device 18 further includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, Novell® NetWare®, and the likes. In aspects, the operating system may be provided by cloud computing.

Computing device 18 includes a storage implemented as one or more physical apparatus used to store data or programs on a temporary or permanent basis. The storage may be volatile memory, which requires power to maintain stored information, or non-volatile memory, which retains stored information even when the computing device 18 is not powered on. In aspects, the non-volatile memory includes flash memory, dynamic random-access memory (DRAM), ferroelectric random-access memory (FRAM), and phase-change random access memory (PRAM). In aspects, the storage may include, by way of non-limiting examples, CD-ROMs, DVDs, flash memory devices, magnetic disk drives, magnetic tapes drives, optical disk drives, solid-state drive, universal serial bus (USB) drive, and cloud computing-based storage. In aspects, the storage may be any combination of storage media such as those disclosed herein.

The computing device 18 further includes a processor, an extension, an input/output device, and a network interface, although additional or alternative components are also contemplated. The processor executes instructions which implement tasks or functions of programs. When a user executes a program, the processor reads the program stored in the storage, loads the program on the RAM, and executes instructions prescribed by the program. Although referred to herein in the singular, it is understood that the term processor includes multiple similar or different processes locally, remotely, or both locally and remotely distributed.

The processor may include a field programmable gate array (FPGA), a digital signal processor (DSP), a central processing unit (CPU), a graphical processing unit (GPU), a microprocessor, application specific integrated circuit (ASIC), and combinations thereof, each of which includes electronic circuitry within a computer that carries out instructions of a computer program by performing the basic arithmetic, logical, control and input/output (I/O) operations specified by the instructions. Those skilled in the art will appreciate that the processor may be substituted for by using any logic processor (e.g., control circuit) adapted to execute algorithms, calculations, and/or set of instructions described herein.

In aspects, the extension may include several ports, such as one or more USBs, IEEE 1394 ports, parallel ports, and/or expansion slots such as peripheral component interconnect (PCI) and PCI express (PCIe). The extension is not limited to the list but may include other slots or ports that can be used for appropriate purposes. The extension may be used to install hardware or add additional functionalities to a computer that may facilitate the purposes of the computer. For example, a USB port can be used for adding additional storage to the computer and/or an IEEE 1394 may be used for receiving moving/still image data.

The network interface is used to communicate with other computing devices, wirelessly or via a wired connection following suitable communication protocols. Through the network interface, computing device 18 may transmit, receive, modify, and/or update data from and to an outside computing device, server, or clouding space. Suitable communication protocols may include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency—embedded millimeter wave transvers optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-2003 standard for wireless personal area networks (WPANs)).

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, C#, Delphi, Fortran, Java, JavaScript, machine code, operating system command languages, Pascal, Perl, PL1, scripting languages, Visual Basic, meta-languages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Continuing with reference to FIG. 5, as noted above, each of the audio sensor devices 19 is connected, via wired or wireless connection, to computing device 18, which in turn, is connected, via wired or wireless connection, to display 17. Display 17 is also connected to third surgical instrument 13 (FIG. 1) directly or via controller 14 (FIG. 1) for processing the video (or other imaging) data obtained by surgical instrument 13 (FIG. 1) and outputting the same for display on display 17, e.g., as a video image.

The audio sensor devices 19 within the internal surgical site "S" are configured to sense audio within the internal surgical site "S" and to communicate the same to computing device 18. Such audio sensed within the internal surgical site "S" may pertain to, for example: operation of the at least one surgical instrument 11, performance of the at least one surgical instrument 11 and tissue effects, procedure information, etc. With respect to operation of the at least one surgical instrument 11, more specifically, the sensed audio may pertain to: manipulation of the at least one surgical instrument 11 for grasping tissue, manipulating tissue, blunt dissection, poke and spread, closure of a jaw member(s) or otherwise clamping tissue, rotation the end effector assembly, articulation of the end effector assembly, etc.; deployment of a knife; firing of a surgical clip applier to form a surgical clip; firing of a surgical stapler to drive staples and/or advance a knife; energization of an electrically conductive tissue contacting surface (e.g., for sealing tissue); energization of an electrode; deployment of an electrode or other energy-based or mechanical component; energization of an electrical or thermal cutting element (e.g., for cutting tissue); and activation of an ultrasonic blade (including a mode of thereof such as, for example a low power mode vs a high power mode).

With respect to performance of the at least one surgical instrument 11 and tissue effects, more specifically, the sensed audio may pertain to: blood flow from a bleeding vessel; generation and/or release of steam during tissue treatment, e.g., sealing; generation and/or release of smoke; popping as a result of arcing or other electrosurgical events; frictional contact between an activated ultrasonic blade and tissue (or the jaw member of the ultrasonic device); mechanical cutting of tissue; release of tension on tissue (from cutting, for example); manipulation of or contact with different types of tissue; treatment (sealing, cutting, etc.) of different types of tissue; treatment quality (effective seal, cut, etc. versus ineffective seal, cut, etc.); sealing tissue without subsequently cutting tissue; cutting tissue that has not been previously (or effectively) sealed; and tissue sealing cycle progress.

With respect to procedure information, more specifically, the sensed audio may pertain to: insertion and/or removal of surgical instruments from the surgical site (including the type of instruments inserted and/or removed); contact between surgical instruments; and location(s) of instruments and/or identified tissue (organs, bones, vessel, etc.).

It is understood that the above is not exhaustive and that many other sounds within an internal surgical site "S" during the course of a surgical procedure therein may be detected. Computing device 18 process the audio data itself or in conjunction with other feedback data to provide a suitable output, e.g., control instruction or display output on display 17. Of course, there will also be noise within the internal surgical site "S" that is detected by audio sensor devices 19; such noise is filtered out by computing device 18 during processing of the audio data.

The audio sensor devices 19 external to the internal surgical site "S" are configured to sense audio externally of the internal surgical site "S" and to communicate the same to computing device 18. Such audio may include, for example: verbal communications between surgeons and/or staff or other information pertaining to the mood or emotional state of the surgical staff (e.g., which may be an indicator of whether the surgery is going as expected, if there are concerns or surprises, etc.); audio produced by mechanical operations of surgical instruments 11 (e.g., actuating a handle, latching or unlatching a handle, firing a trigger, depressing a button, actuating a rotation wheel or articulation control, etc.); audible tones produced by surgical instruments 11 and/or generator 15 (FIG. 1) (e.g., error tones, activation tones, seal complete tones, etc.); contact between surgical instruments 11; insertion, manipulation, and/or removal of surgical instruments into/from the internal surgical site "S;" etc. It is understood that the above is not exhaustive and that many other sounds external to an internal surgical site "S" during the course of a surgical procedure may be detected. Computing device 18 processes the audio data itself or in conjunction with other feedback data to provide a suitable output, e.g., control instruction or display output on display 17. Of course, there will also be noise external of the internal surgical site "S" that is detected by audio sensor devices 19; such noise is filtered out by computing device 18 during processing of the audio data.

The feedback data utilized together with the internal and/or external audio sensor data may include, for example, feedback data from any connected sensor, generator, and/or other surgical instrument. Such feedback data may include sensor data such as, for example, data from an electrical (impedance) sensor; an accelerometer; an imaging sensor (video, thermal, ultrasound, etc.); an actuation sensor (e.g., sensing a position or state of actuation of a handle, trigger, button, etc.); a location sensor (e.g., GPS sensor); a jaw aperture sensor; and the like. Such feedback data may also include, for example, generator feedback data (voltage, current, seal cycle progress, etc.), motor torque data, etc. Additionally, previous data and/or temporal data may be utilized to correlate sensed audio data, feedback data, and/or other data such as, for example, to enable determination of: sealing without cutting; cutting without sealing; multiple cut actuations/activations; multiple seal activations; and clamping and re-clamping.

Figure 6:
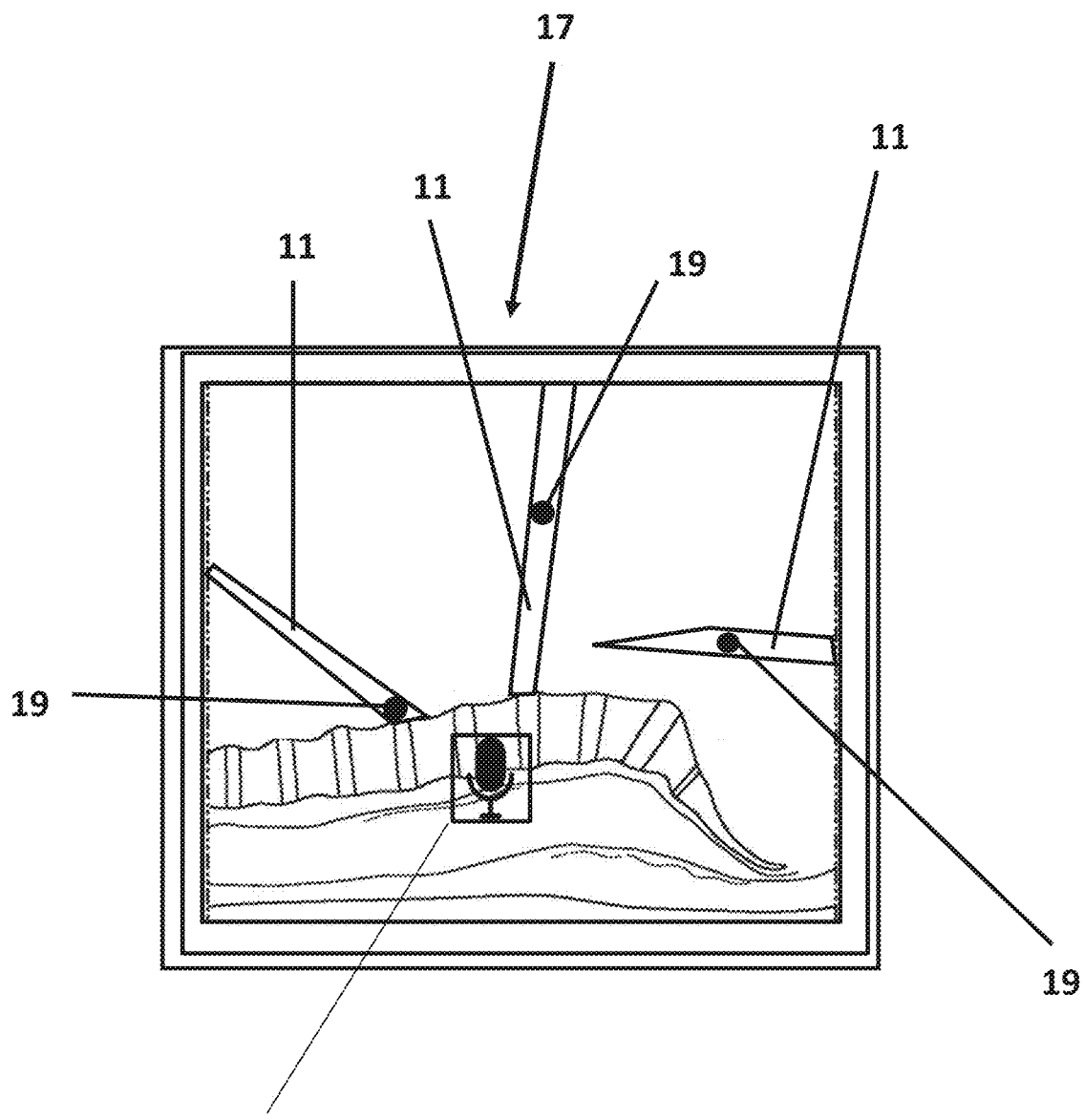
FIG. 6 is a graphical representation of a display provided in accordance with the present disclosure shown displaying video image data of an internal surgical site and audio location data overlaid on the video image data.

With additional reference to FIG. 6, where multiple audio sensor devices 19 are provided, due to differences in the configurations (frequency ranges, for example) and/or positions of the audio sensor devices 19, different sounds, different magnitudes of the same sounds, and/or different time of arrival measurements for sounds may be obtained to enable localization. This enables computing device 18 to perform sound localization of the audio data obtained from the various audio sensor devices 19 in order to determine a location of a particular sound or sounds. The location may then be indicated, for example, as an icon 600 overlaid on the video image of the internal surgical site displayed on display 17 at the location from which the sound is determined to emanate. This information alone, or together with reproduction of the filtered audio output by computing device 18 (e.g., to a speaker, a user's headphones, etc.), allows the user to hear (absent of or with reduced noise) the audio of interest in real-time (which may be amplified, isolated, or otherwise processed), and also to visualize a location where that audio is coming from within the internal surgical site "S." For example, as illustrated in FIG. 6, audio may be detected as a result of contact between two of the surgical instruments 11 where the point of contact is obstructed from view by tissue. In this instance, the location of the display icon 600, alone or together with the sound itself (e.g., which may be a clang, squealing, etc.), provides information to the user to enable the user to determine that the cause of the sound was contact between two of the surgical instruments 11 and where the contact occurred. In aspects, the audio data processing may further be utilized to graphically or textually select, modify, or otherwise provide a suitable display icon 600 such as, for example, based on a magnitude of the sound, a type of sound, a category of sound, a location of the sound, etc., to further inform the user.

Figure 7:
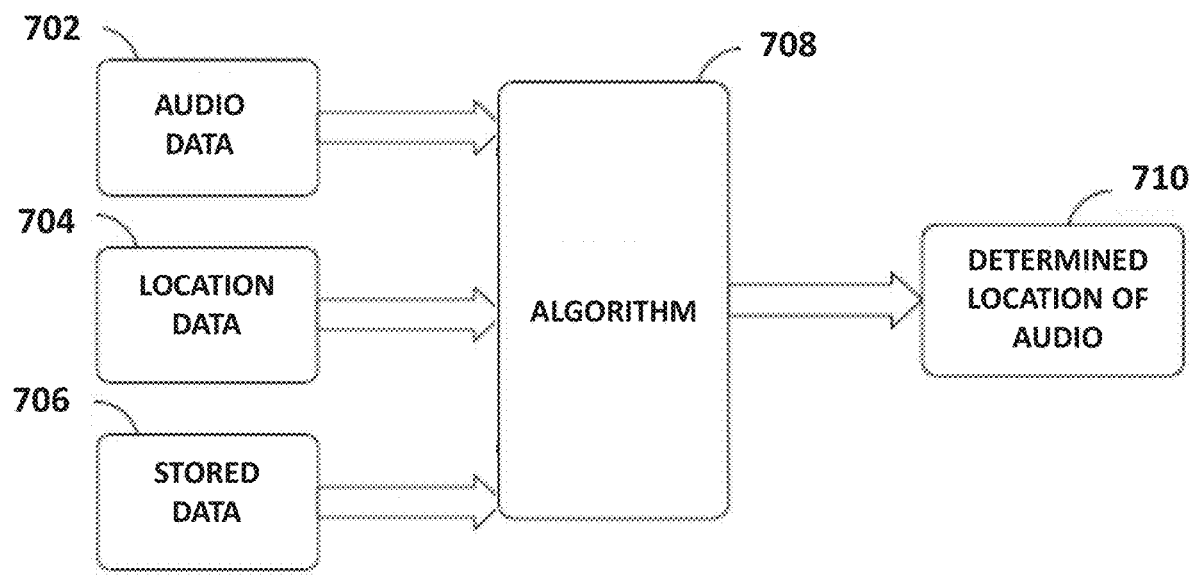
FIGS. 7 and 8 are logic diagrams of algorithms provided in accordance with the present disclosure.

Referring to FIG. 7, in conjunction with FIGS. 1 and 5, in aspects, the at least one surgical instrument 11 and/or at least one audio sensor device 19 (whether standalone or incorporated into surgical instrument(s) 11) may include a location sensor such as, for example, a proximity sensor, a GPS sensor, an RFID tag, etc. to enable relative or absolute determination of a location of the at least one surgical instrument 11 and, more particularly, relative or absolute determination of a location of a particular portion thereof, e.g., the end effector assembly, the audio sensor device 19, etc. Alternatively or additionally, location information may be obtained via video image processing based on video data from surgical instrument 13 (FIG. 1), or in any other suitable manner. Regardless of the manner in which location information is obtained, the location data 704 is input, together with the obtained audio data 702 from the audio sensor device(s) 19 and stored data 706 stored on computing device 18, to an algorithm 708, e.g., implemented on computing device 18, in order to output a determined location of the audio 710, e.g., for display (as an icon or in any other suitable manner) on display 17. The stored data 706 may include, for example a catalogue of known sounds from which all other sounds can be filtered out and/or from which particular sounds can be identified by matching, comparison, etc. The stored data 706 may additionally or alternatively include information about the patient, the procedure to be performed, the instruments utilized, etc., which may provide information regarding the potential sounds that may be encountered. In aspects, algorithm 708 includes one or more machine learning algorithms.

Figure 8:
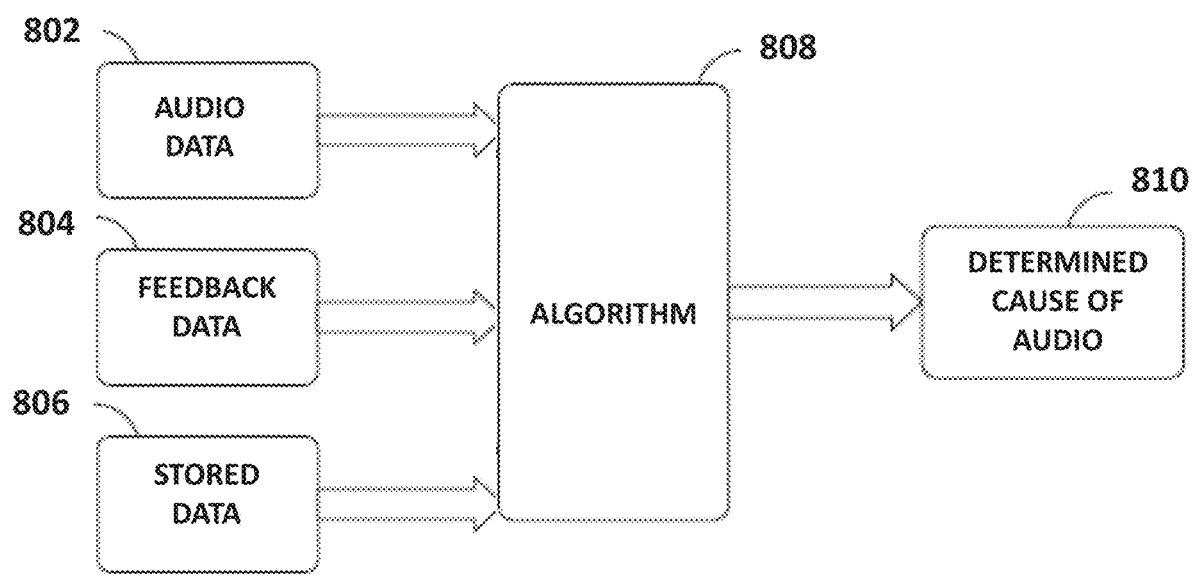

Turning to FIG. 8, in conjunction with FIGS. 1 and 5, in aspects, in addition to inputting the audio data 802 into an algorithm 808, additional feedback data 804 from the at least one surgical instrument 11, surgical generator 15, and/or other devices of or associated with surgical system 10 may be input to the algorithm 808 along with stored data 806. For example: location data such as detailed above may be input into or determined by computing device 18; information pertaining to the activation of energy, a type of activation (energy modality, mode, power level, etc.), energy delivery parameters, tissue feedback data (such as impedance), a status of energy delivery (e.g., tissue sealing complete, tissue cutting complete, a phase of tissue sealing, etc.), and/or other data relating to the activation of energy by one or more of the surgical instruments 11 may be provided from the surgical instrument 11 or generator 15 to computing device 18; and/or information pertaining to mechanical actuation of one or more of the surgical instruments 11 may be provided from the surgical instrument 11 to computing device 18 such as, for example, actuation of a handle or lever to grasp tissue and/or the approximation of one or more jaw members to grasp tissue, actuation of a trigger to fire a mechanical knife and/or the movement of the knife upon firing thereof, actuation of a handle or lever to fire a clip applying device or surgical stapler and/or firing of the clip applying device or surgical stapler, etc.

The stored data 806 may include, for example a catalogue of known sounds and/or data correlating known feedback events (such as those provided by the feedback data 804 detailed above) with corresponding sounds. The stored data 806 may additionally or alternatively include information about the patient, the procedure to be performed, the instruments utilized, etc., which may provide information regarding the potential sounds that may be encountered.

Regardless of the particular feedback and/or stored data 804, 806, respectively, the feedback data 804 is input, together with the obtained audio data 802 from the audio sensor devices 19 and stored data 806 stored on computing device 18, to algorithm 808, e.g., implemented on computing device 18, in order to output a determined cause of the audio 810, e.g., for display (as an icon or in any other suitable manner) on display 17, to provide a suitable alert in the event of an error condition, to provide a suitable alert upon completion of an activation or actuation, etc. In aspects, algorithm 808 includes one or more machine learning algorithms. Further, in aspects, algorithms 708 (FIG. 7) and 808 are incorporated into a single algorithm or utilized together to enable determination of a location and cause of a particular sound detected.

Figure 9:
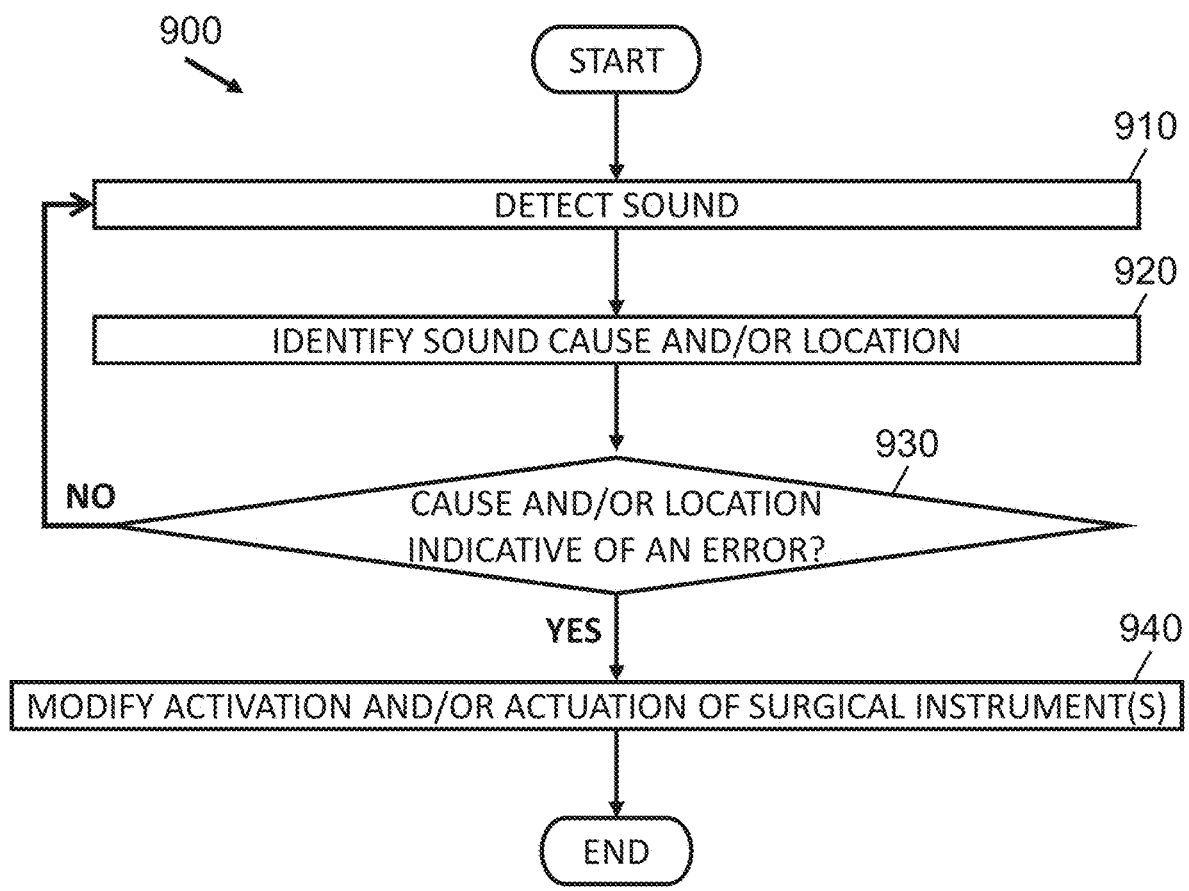
FIG. 9 is a flow diagram of a method provided in accordance with the present disclosure.

Referring to FIG. 9, in conjunction with FIGS. 1 and 5, in addition or as an alternative to utilizing the determined location and/or cause of audio to provide a display or other suitable output to the user, such information may be utilized in controlling one or more components of surgical system 10, e.g., by modifying the activation and/or actuation of one or more of surgical instruments 11. More specifically, as illustrated in method 900 of FIG. 9, initially, sound is detected at step 910, e.g., as detailed above. The detected sound is then processed, e.g., as detailed above, to identify the cause of the sound and/or a location of the sound at step 920 (including filtering of noise from the detected sound). Based upon the identified cause and/or location of the sound, either alone or in combination with other data, e.g., such as any of the feedback and/or stored data detailed above, the method determines at step 930 whether the cause and/or location of the sound is indicative of a potential error. For example, the stored data may include a list of sounds, causes, and/or magnitude levels that correspond to potential error conditions. If a potential error condition is detected, "YES" at step 930, the method proceeds to step 940 wherein the activation (supply of energy) and/or actuation (mechanical actuation) of one or more of surgical instruments 11 is modified, e.g., inhibited, reduced, etc. For example, where a potential error is detected with respect to an energy-based instrument, energy supply to that instrument may be inhibited or the instrument may only be capable of operating in a low energy setting mode. As another example, where a potential error is detected with respect to a mechanical instrument, mechanical actuation, e.g., firing of staples, grasping of tissue, firing of a cutting element, firing of a surgical clip may be inhibited. If no potential error condition is detected, "NO" at step 930, the method returns to step 910 to continue monitoring sounds for potential errors. Although detailed above with respect to an error condition, it is understood that method 900 may likewise apply to identifying causes and/or locations of sounds as indicative of other conditions and controlling one or more surgical instruments 11 based on the detection of such conditions.

Although the above is detailed with respect to audio sensing, the present disclosure may additionally or alternatively be implemented using accelerometers, e.g., 3-axis accelerometers, in similar locations to enable detection of vibrations (that may be at lower frequencies than audio frequencies) in order to determine types and/or locations of vibrations and to provide feedback and/or enable control based thereon.

Audio and/or vibration sensing, such as detailed above, may additionally or alternatively be utilized to detect body pulse and/or blood flow. The detection of blood flow, for example, may be utilized to detect and localize blood vessels (including whether the blood vessel is intact or bleeding), determine whether blood vessels have been completely sealed, determine whether prior seals are leaking, etc. Detection of body pulse (and/or breathing) may be utilized, for example, to facilitate stabilization of robotic devices and/or to provide such information on a visual display to enable the user to account for the movement of tissue during respiration, to detect blood flow and/or the condition of a blood vessel (sealed, incomplete seal, etc.). With respect to detection of complete or incomplete vessel seals, feedback-based control may re-initiate a sealing cycle, inhibit cutting of incompletely sealed vessels, etc.

Audio and/or vibration sensing, such as detailed above, may additionally or alternatively be utilized to detect changes in ultrasonic dissector performance, ultrasonic jaw liner contact, bad staple lines, poorly formed staples, motor torque, etc. and, in aspects, feedback regarding the same may be utilized to alert the user, control operation, etc.

Vibration sensing may further be utilized, alone or together with audio sensing, to detect instrument rotation, bending, and/or stress, and/or tissue tension, stress, etc. Further still, vibration and/or audio sensing may enable detection of jaw closure (and, in aspects, the extent thereof), pressure on grasped tissue, button presses/activations, etc.

Audio sensing may also be utilized to capture surgeon and/or staff voices for use in providing feedback and/or control, or may anonymize, obscure, blur, delete, and/or otherwise filter (for example, as part of the noise filtering or as another filtering process) out human voices such that the surgeon and/or staff cannot be identified from the audio data and/or such that speech cannot be recognized (while tone, inflection, etc. may still be recognizable or may also be filtered out).

Detected audio, once processed and/or filtered, may be played back to the surgeon in real time or near real time through headphones to give directional ques to the surgeon, in addition to or as an alternative to visual ques such as those detailed above. Such audio directional ques may be provided based upon location and/or heading information of the surgeon, e.g., where the directional ques change based on the surgeon's location and/or facing direction (where the surgeon's head is pointing).

In additional or alternative aspects, the detected audio may be replaced with proxies such that the actual sensed sounds are changed to different sounds that are more readily identifiable or distinguishable by the surgeon. For example, bubbling and popping could be replaced with long and short beeps, respectively.

Further still, audio and/or vibration sensing may be utilized to detect the sounds and/or vibrations associated with electrosurgical arcing, burning, an arc signature in the voltage and current electrosurgical waveforms, etc. outside an expected area or location or the field of view of the video feed, thus indicating that energy is being delivered somewhere outside the surgeon's view. Energy may be stopped in such instances and/or an alert may be provided to the user notifying regarding the same.

Figure 10:
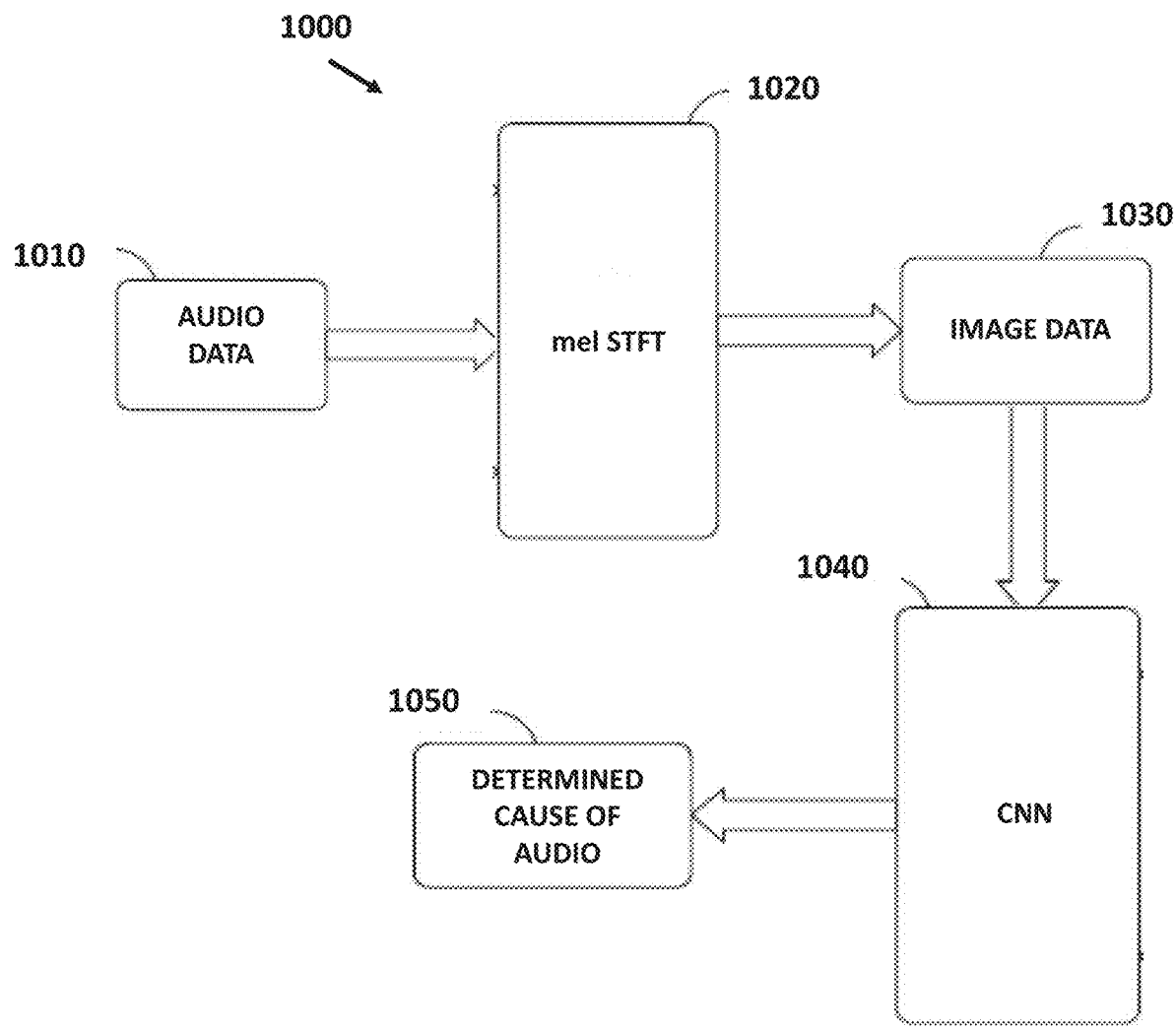
FIG. 10 is a logic diagram of another algorithm provided in accordance with the present disclosure.
Figure 11A:
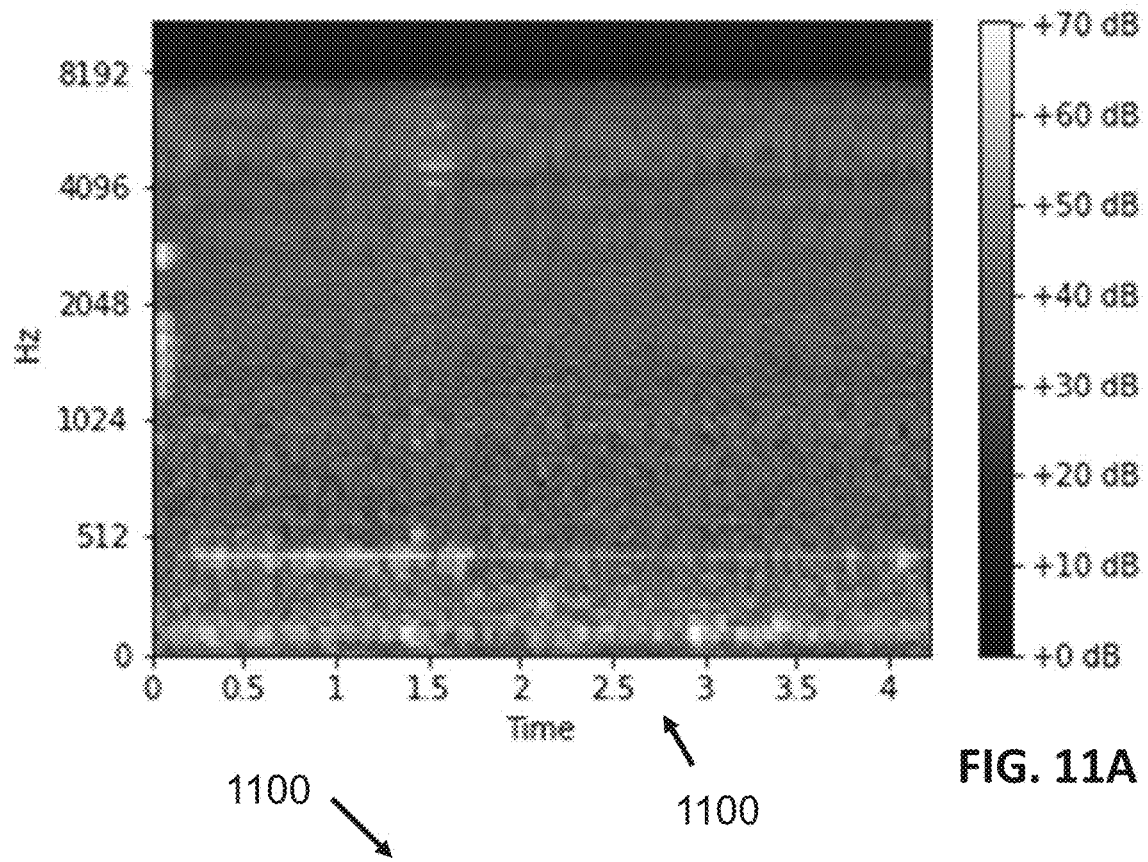
FIGS. 11A-11D are images of exemplary melody spectrograms in accordance with the present disclosure.
Figure 11B:
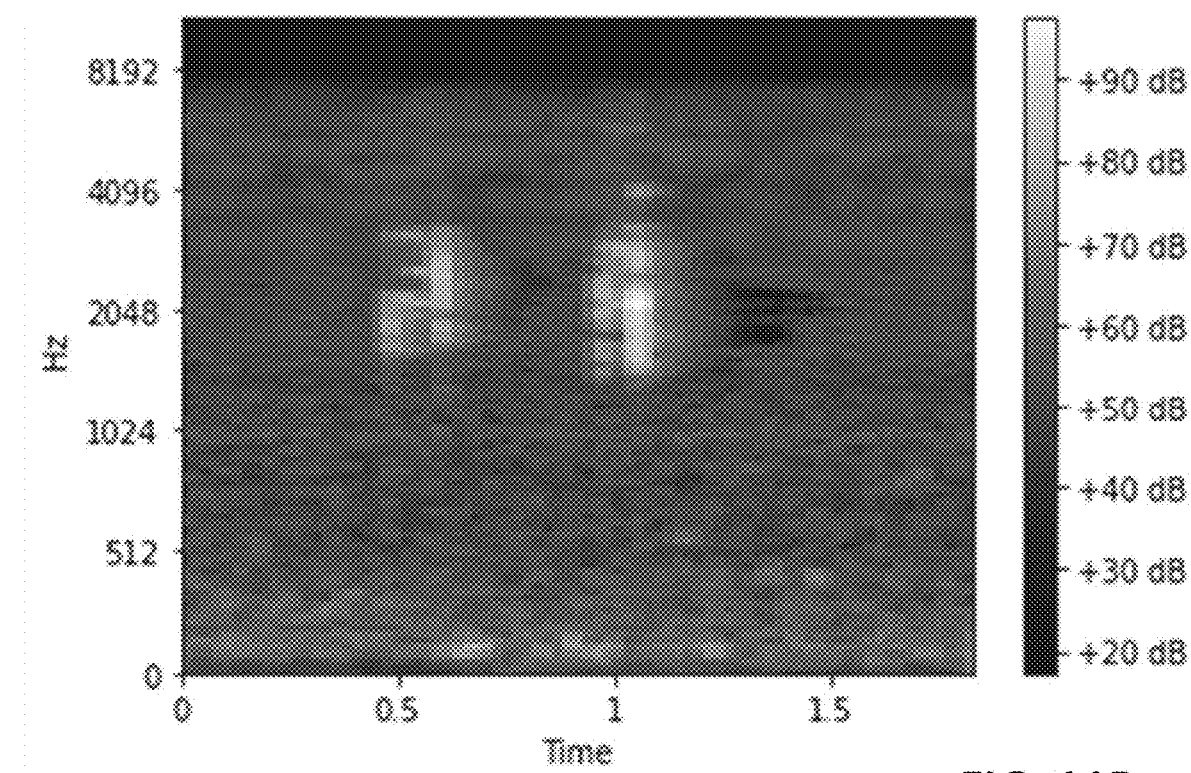
Figure 11C:
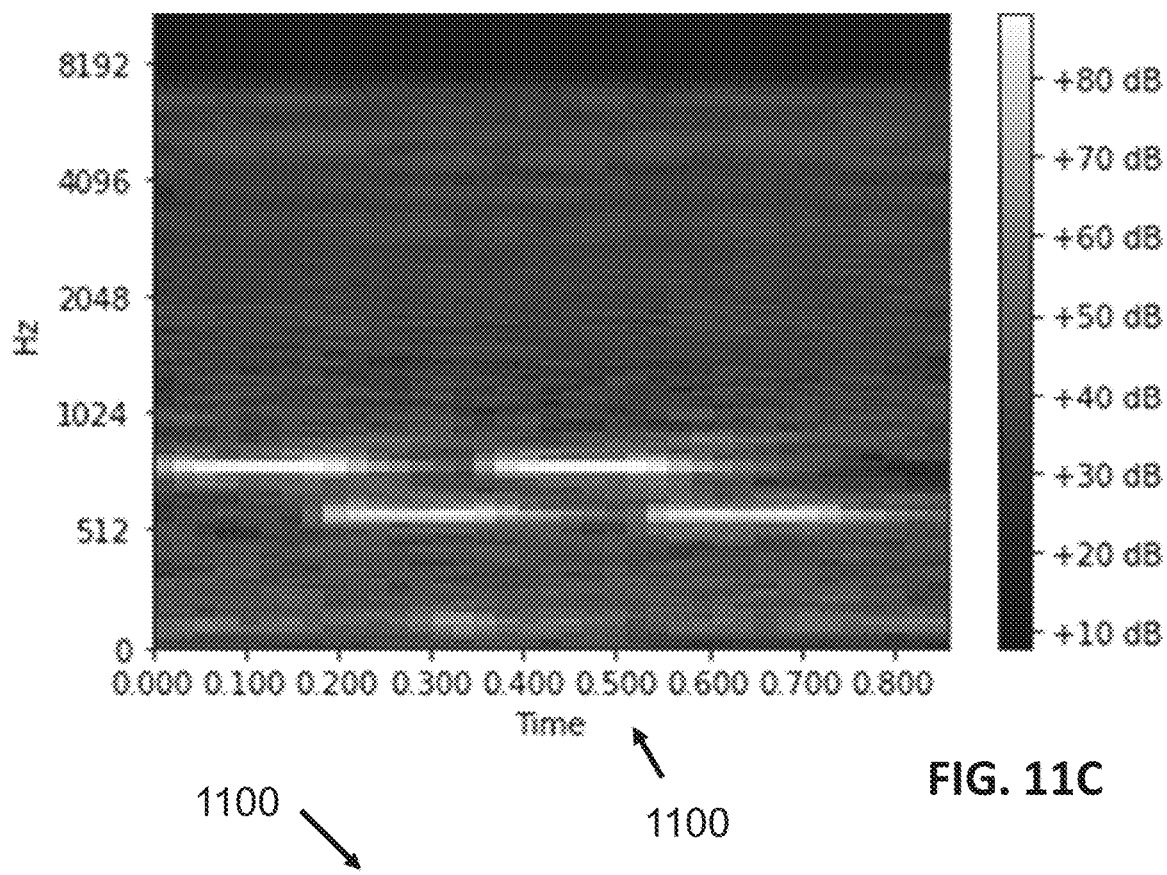
Figure 11D:
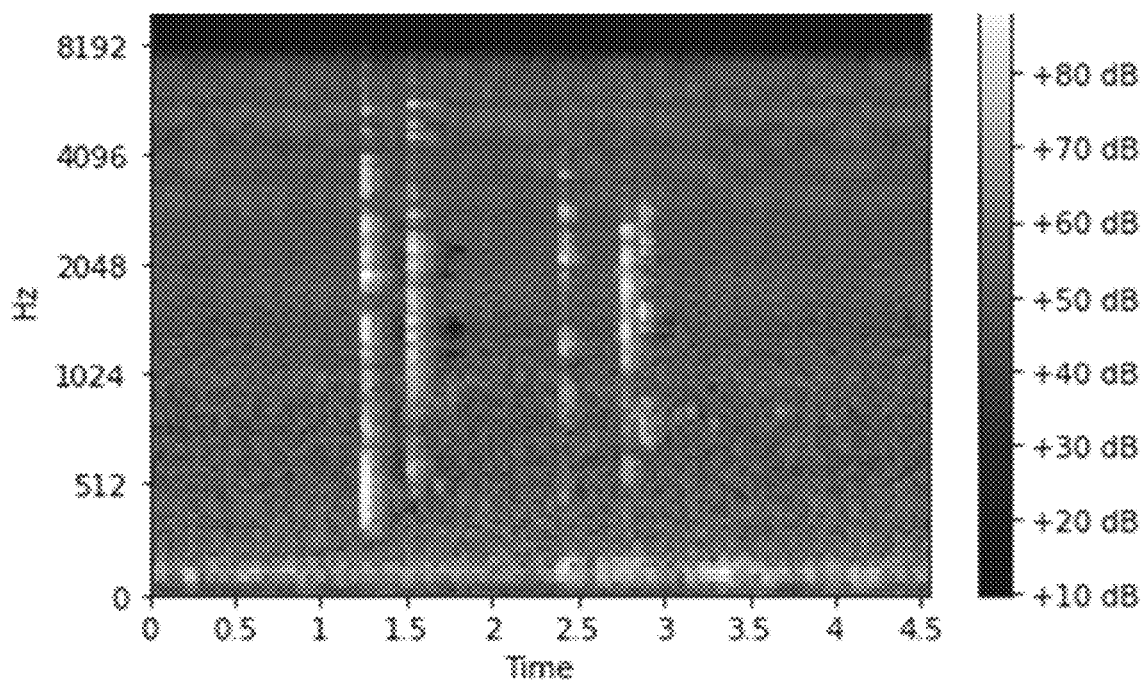
Figure 12:
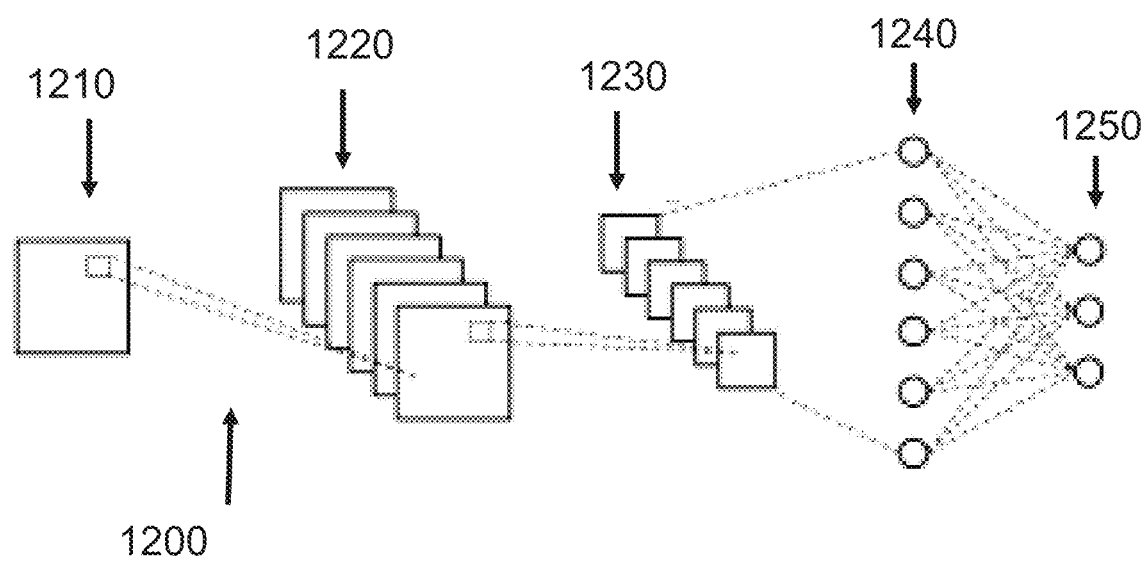
FIG. 12 is a schematic illustration of a convolutional neural network (CNN) configured for use in accordance with the present disclosure.

Turning to FIGS. 10-12, as detailed above, machine learning may be utilized to facilitate determination of a location of audio data (see FIG. 7) and/or a cause of audio data (see FIG. 8). In particular, machine learning may be utilized by implementing one or more of: supervised learning, semi-supervised learning, unsupervised learning, reinforcement learning, association rule learning, decision tree learning, anomaly detection, feature learning, etc., and may be modeled as one or more of a neural network, Bayesian network, support vector machine, genetic algorithm, etc. The machine learning algorithm(s) may be trained based on empirical data and/or other suitable data and may be trained prior to deployment for use during a surgical procedure or may continue to learn based on usage data after deployment and use in a surgical procedure(s).

With respect to neural networks, convolutional neural networks (CNNs) are generally accepted as very efficient and effective deep learning algorithms. However, CNNs are utilized in computer vision or image processing machine learning applications, where image data is provided as the input to the CNN. Thus, in order to take advantage of the benefits of CNNs, the audio data obtained in accordance with the present disclosure must first be converted to image data that can be input to a CNN to enable determination of, for example, the cause of the audio.

More specifically, and with reference to FIG. 10, an algorithm 1000 in accordance with the present disclosure receives audio data 1010 that is input to a conversion algorithm such as, for example, a melody Short-Time Fourier Transform (mel STFT) 1020, that, in turn, outputs image data 1030 based on the input audio data 1010. The output image data 1030 may be, for example, image data representing a melody spectrogram 1100 (FIGS. 11A-11D). Various different melody spectrograms 1100 based on different surgical audio data are illustrated, for example, in FIGS. 11A-11D. However, other suitable transformations of the audio data to image data are also contemplated. Once the audio data 1010 is converted into image data 1030, the image data 1030 can be input to the CNN 1040. The CNN 1040, in turn, outputs a determined cause of the audio 1050 based on processing of the image data 1030.

Algorithm 1000 may be implemented on computing device 18 (FIGS. 1 and 5), on any other suitable device, or across multiple devices. Further, the determined cause of the audio 1050 output from algorithm 1000 may be displayed (as an icon or in any other suitable manner) on display 17 (FIGS. 1 and 5), may be output as an audible, visual, tactile, and/or other suitable output to the user indicating the determined cause, may be used in feedback-based control of the at least one surgical instrument 11, generator 15, and/or other devices (see FIG. 1), and/or may be utilized in any of the manners detailed above or in any other suitable manner. Algorithm 1000 may further utilize additional input data to facilitate determining the cause of the audio such as, for example, feedback data, location data, and/or stored data, similarly as detailed above with respect to the algorithms of FIGS. 7 and 8, respectively.

In aspects, audio data 1010 may be pre-processed prior to input to algorithm 1000 (as may the audio data associated with any other aspects of the present disclosure prior into the corresponding algorithms). More specifically, a stream of audio data received from the one or more audio sensors 19 (FIG. 1), e.g., in real time, may be processed to determine one or more sounds of interest within the audio data stream, e.g., using filtering, amplification, isolation, transformation, and/or other suitable audio processing techniques. The portion or portions of the stream of audio data including the one or more sounds of interest may then be input to algorithm 1000 as the audio data 1010, thus avoiding algorithm 1000 (and CNN 1200 in particular) processing data that does not or is not likely to include sound(s) of interest, thereby reducing computational time. The sampling rate may also be selected to achieve a balance between computational speed and sufficient granularity of data obtained. The portion or portions of the stream of audio data input to algorithm 1000 may alternatively or additionally be determined based on other data such as, for example, feedback data, stored data, location data, etc. For example, the portion or portions of the stream of audio data input to algorithm 1000 may be selected based upon a temporal relation (before, during, within a determined period after, etc.) to actuation, activation, or manipulation of a surgical instrument. In other aspects, the entire stream of audio data is input as the audio data 1010.

Referring to FIG. 12, an exemplary CNN 1200 is shown. CNN 1200, as noted above, is configured to receive image data as an input. With momentary reference to FIG. 10, the image data provided to CNN 1200 may be, as detailed above, the image data 1030 representative of a melody spectrogram 1100 (FIGS. 11A-11D) produced by converting the sensed audio data 1010 into image data 1030, e.g., using mel STFT 1020. Other suitable image data 1030 based on the sensed audio data 1010 is also contemplated. The image data 1030 may be provided corresponding to a color image (RGB) or may first be converted to correspond to a grayscale image (e.g., to facilitate processing).

Continuing with reference to FIG. 12, CNN 1200 includes an input layer 1210 (configured to receive the input image data), one or more convolutional layers 1220, one or more pooling layers 1230, one or more fully connected layers 1240, and an output layer 1250 configured to output a determination of the cause of the audio. In aspects, a flatten layer (not explicitly shown) is disposed between the layer (the final pooling layer 1230 or final convolutional layers 1220) and the first fully connected layer 1240. Further, a pooling layer 1230 may be disposed after each convolutional layer 1220 or a set of convolutional layers 1220. In other configurations, pooling layer 1230 is omitted.

The one or more convolutional layers 1220 may implement any suitable similar or different activation functions (e.g., ReLU or Tanh). Further the one or more convolutional layers 1220 may include any suitable number of kernels, e.g., 32, 64, or 128; may implement a Sobel filter or other suitable filter; may utilize any suitable filter size, e.g., 3×3, 5×5, or 7×7; and/or may utilize any suitable stride, e.g., 1 or 2. Padding, e.g., of 1 or 2, may also be utilized, in aspects.

The one or more pooling layers 1230 may be similar or different and may utilized, for example, max pooling or average pooling.

The one or more fully connected layers 1240 may use any suitable similar or different activation functions (e.g., ReLU or Tanh). The output layer 1250 provides a classification output such as, for example, the determined cause of the audio, as the most likely cause or, in aspects, one or more causes with probabilities for each. The activation function used at the output layer 1250 may be, for example, the sigmoid function or softmax. CNN 1200 may be tuned (learn) to optimize the hyperparameters and/or in any other suitable manner to improve performance thereof. Learning using CNN 1200 may be completed prior to deployment for use, e.g., in surgical procedures, or may be updated throughout use in surgical procedures periodically or continuously, using data specific to the surgical system employing CNN 1200 or data across multiple surgical systems employing CNN 1200.

Referring back to FIG. 10, in aspects, algorithm 1000 is configured to operate substantially in real-time (taking into account processing time) so as to provide the output of the determined cause of the audio in substantially real-time upon sensing the audio.

While several aspects of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope of the claims appended hereto.

What is claimed is:

1. A surgical system, comprising:
   at least one audio sensor disposed on a surgical device having at least one jaw member, the at least one audio sensor configured to sense audio during a surgical procedure and to output audio data based on the sensed audio; and
   a computing device operably coupled to the at least one audio sensor and configured to receive the output audio data from the at least one audio sensor, the computing device including a processor and memory storing instructions that, when executed by the processor, cause the processor to:
      determine a location of a sound with respect to the surgical device based at least on the output audio data; and
      output an indication of the location of the sound.

2. The surgical system according to claim 1, wherein the processor is caused to determine the location of the sound within an internal surgical site based on the output audio data, and wherein outputting the indication of the location of the sound includes displaying, on a display providing a video image of the internal surgical site, an icon overlaid over the video image of the internal surgical site at a location on the video image corresponding to the location of the sound.

3. The surgical system according to claim 1, wherein the processor is caused to determine a cause of the sound and wherein outputting the indication includes outputting an indication of the cause of the sound.

4. The surgical system according to claim 1, wherein:
   the at least one audio sensor is a first audio sensor of a plurality of audio sensors, the plurality of audio sensors including a second audio sensor; and
   the first audio sensor is disposed within an internal surgical site and the second audio sensor is disposed external of the internal surgical site.

5. The surgical system according to claim 1, wherein the processor is caused to determine a cause or the location of the sound based on the output audio data and additional data including at least one of: stored data, location data, or feedback data.

6. The surgical system according to claim 1, wherein the processor is caused to convert at least a portion of the output audio data into image data and to determine a cause of the sound based on the image data.

7. The surgical system according to claim 1, wherein the at least one audio sensor is disposed on a jaw member of the surgical device.

8. The surgical system according to claim 1, wherein the at least one audio sensor is disposed externally on the surgical device.

9. A surgical system, comprising:
   a plurality of audio sensors, at least one audio sensor of the plurality of audio sensors coupled to a surgical device having at least one jaw member, the at least one audio sensor configured for positioning within an internal surgical site, at least one other audio sensor of the plurality of audio sensors configured for positioning external of the internal surgical site, each audio sensor of the plurality of audio sensors configured to sense audio and to output audio data based on the sensed audio; and
   a computing device operably coupled to the plurality of audio sensors and configured to receive the output audio data from each audio sensor of the plurality of audio sensors, the computing device including a processor and memory storing instructions that, when executed by the processor, cause the processor to:
      determine a location of a sound with respect to the surgical device based at least on the output audio data; and
      control operation of at least one surgical instrument based on the determined location of the sound.

10. The surgical system according to claim 9, wherein at least one audio sensor of the plurality of audio sensors is disposed on a jaw member of the surgical device.

11. The surgical system according to claim 9, wherein the processor is caused to determine both a cause and the location of the sound based at least on the output audio data.

12. The surgical system according to claim 9, wherein the processor is caused to determine the location of the sound based on the output audio data and additional data including at least one of: stored data, location data, or feedback data.

13. The surgical system according to claim 9, wherein the processor is caused to convert at least a portion of the output audio data into image data and to determine a cause of the sound based on the image data.

14. The surgical system according to claim 9, wherein the processor is caused to control operation of the at least one surgical instrument by outputting a signal to inhibit actuation or activation of the at least one surgical instrument.

15. A surgical system, comprising:
   at least one audio sensor coupled to a surgical device configured to sense audio during a surgical procedure and to output audio data based on the sensed audio; and
   a computing device operably coupled to the at least one audio sensor and configured to receive the output audio data from the at least one audio sensor, the computing device including a processor and memory storing instructions that, when executed by the processor, cause the processor to:
      convert at least a portion of the output audio data into image data;
      determine a location of a sound with respect to the surgical device based on the image data; and output at least one of an indicator or a control signal based on the determined location of the sound.

16. The surgical system according to claim 15, wherein converting the at least a portion of the output audio data into the image data includes applying a melody Short-Time Fourier Transform to the at least a portion of the output audio data to obtain a melody spectrogram as the image data.

17. The surgical system according to claim 15, wherein the processor is caused to determine a cause of the sound based on the image data by implementing a convolutional neural network (CNN).

18. The surgical system according to claim 17, wherein the processor is caused to output the control signal based on the determined cause of the sound, the control signal configured to at least one of: inhibit actuation of at least one surgical instrument, inhibit activation of the at least one surgical instrument, or change an operating parameter of the at least one surgical instrument.

19. The surgical system according to claim 15, wherein the processor is caused to select the at least a portion of the output audio data to be converted, the selection based at least on a detection of the sound.

20. The surgical system according to claim 15, wherein the processor is caused to select the at least a portion of the output audio data to be converted, the selection based at least on additional input data.

* * * * *